US010063814B2

(12) United States Patent
Wood et al.

(10) Patent No.: US 10,063,814 B2
(45) Date of Patent: Aug. 28, 2018

(54) SMOKING ARTICLE PACKAGE INSPECTION SYSTEM AND ASSOCIATED METHOD

(71) Applicant: R.J. Reynolds Tobacco Company, Winston-Salem, NC (US)

(72) Inventors: Gary Lee Wood, Rural Hall, NC (US); Chris Campbell, Jonesville, NC (US); Hung Phan, Clemmons, NC (US); Hugh Gates, Winston-Salem, NC (US); Jim Belk, King, NC (US); Zach Francis, High Point, NC (US); Reginald Thomas, Tobaccoville, NC (US); Luke Hutchens, East Bend, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 486 days.

(21) Appl. No.: 14/205,818

(22) Filed: Mar. 12, 2014

(65) Prior Publication Data
US 2015/0264319 A1 Sep. 17, 2015

(51) Int. Cl.
B65B 19/30 (2006.01)
H04N 7/18 (2006.01)
(Continued)

(52) U.S. Cl.
CPC ............. *H04N 7/181* (2013.01); *B65B 19/30* (2013.01); *G01N 21/95* (2013.01); *G06T 7/0004* (2013.01);
(Continued)

(58) Field of Classification Search
CPC ... G06T 7/0004; G06T 7/0006; G06T 7/0008; G06T 7/001; G06T 2207/30144;
(Continued)

(56) References Cited

U.S. PATENT DOCUMENTS 3,288,147 A 11/1966 Molins et al.
3,301,454 A 1/1967 Wayne et al.
(Continued)

FOREIGN PATENT DOCUMENTS

CN 1276999 12/2000
CN 1468068 1/2004
(Continued)

OTHER PUBLICATIONS

International Search Report and Written Opinion of the International Searching Authority for corresponding International Application No. PCT/US2015/019715 dated May 15, 2015.
(Continued)

*Primary Examiner* — Geoffrey E Summers
(74) *Attorney, Agent, or Firm* — Womble Bond Dickinson (US) LLP

(57) ABSTRACT

A smoking article package inspection system configured to inspect a smoking article package is provided. The system includes imaging devices configured to capture images of the smoking article package and an analysis unit configured to analyze the images captured by the imaging devices and determine whether the smoking article package is defective. The imaging devices may be positioned and configured to capture images of the smoking article package at least one of: before and after enclosing a plurality of smoking articles in the smoking article package, before and after printing an identifier on the smoking article package, and before and after wrapping the smoking article package with an outer wrapper. A related method is also provided.

26 Claims, 26 Drawing Sheets

(51) Int. Cl.
*G06T 7/00* (2017.01)
*G01N 21/95* (2006.01)
*B65B 19/20* (2006.01)
*B65B 61/02* (2006.01)
*G01N 21/952* (2006.01)

(52) U.S. Cl.
CPC ............. *B65B 19/20* (2013.01); *B65B 61/025* (2013.01); *G01N 21/952* (2013.01); *G06T 2207/30144* (2013.01)

(58) Field of Classification Search
CPC .......... G06T 2207/30108; G01N 21/95; G01N 21/952; B65B 61/025; B65B 19/00–19/32; H04N 7/181
USPC .......................................... 382/110, 141, 143
See application file for complete search history.

(56) References Cited

U.S. PATENT DOCUMENTS

| | | |
|---|---|---|
| 3,308,600 A | 3/1967 | Erdmann et al. |
| 3,366,121 A | 1/1968 | Carty |
| 3,398,675 A | 8/1968 | Potter et al. |
| 3,424,172 A | 1/1969 | Neurath |
| 3,428,049 A | 2/1969 | Leake et al. |
| 3,444,517 A | 5/1969 | Rabinow |
| 3,550,508 A | 12/1970 | Wartman, Jr. |
| 3,550,598 A | 12/1970 | McGlumphy et al. |
| 3,575,276 A | 4/1971 | Rupert |
| 3,602,231 A | 8/1971 | Dock |
| 3,685,521 A | 8/1972 | Dock |
| 3,818,223 A | 6/1974 | Gibson et al. |
| 3,884,246 A | 5/1975 | Walker |
| 3,915,176 A | 10/1975 | Heitmann et al. |
| 4,053,056 A | 10/1977 | Day |
| 4,083,460 A | 4/1978 | Venturi |
| 4,171,739 A | 10/1979 | Yamato |
| 4,174,719 A | 11/1979 | Martin et al. |
| 4,238,993 A | 12/1980 | Brand et al. |
| 4,280,187 A | 7/1981 | Reuland et al. |
| 4,281,670 A | 8/1981 | Heitmann et al. |
| 4,281,671 A | 8/1981 | Byrne et al. |
| 4,284,088 A | 8/1981 | Brand et al. |
| 4,291,713 A | 9/1981 | Frank |
| 4,294,353 A | 10/1981 | Focke et al. |
| RE30,964 E | 6/1982 | Butner et al. |
| 4,403,620 A | 9/1983 | Joseph et al. |
| 4,445,520 A | 5/1984 | Knight et al. |
| 4,474,190 A | 10/1984 | Brand |
| 4,534,463 A | 8/1985 | Bouchard |
| 4,574,816 A | 3/1986 | Rudszinat |
| 4,715,497 A | 12/1987 | Focke et al. |
| 4,736,754 A | 4/1988 | Heitmann et al. |
| 4,781,203 A | 11/1988 | La Hue |
| 4,807,809 A | 2/1989 | Pryor et al. |
| 4,811,745 A | 3/1989 | Cohen et al. |
| 4,844,100 A | 7/1989 | Holznagel |
| 4,850,301 A | 7/1989 | Greene, Jr. et al. |
| 4,852,734 A | 8/1989 | Allen et al. |
| 4,862,905 A | 9/1989 | Green, Jr. et al. |
| 4,878,506 A | 11/1989 | Pinck et al. |
| 4,889,144 A | 12/1989 | Tateno et al. |
| 4,920,990 A | 5/1990 | Lawrence et al. |
| 4,925,602 A | 5/1990 | Hill et al. |
| 4,972,494 A * | 11/1990 | White .................... B65B 19/28 209/535 |
| 5,012,823 A | 5/1991 | Keritsis et al. |
| 5,012,829 A | 5/1991 | Thesing et al. |
| 5,025,814 A | 6/1991 | Raker |
| 5,060,664 A | 10/1991 | Siems et al. |
| 5,060,665 A | 10/1991 | Heitmann |
| 5,074,320 A | 12/1991 | Jones, Jr. et al. |
| 5,101,609 A * | 4/1992 | Cook ...................... B65B 19/32 209/535 |
| 5,101,839 A | 4/1992 | Jakob et al. |
| 5,105,838 A | 4/1992 | White et al. |
| 5,131,416 A | 7/1992 | Gentry |
| 5,139,140 A | 8/1992 | Burrows et al. |
| 5,156,169 A | 10/1992 | Holmes et al. |
| 5,159,944 A | 11/1992 | Arzonico et al. |
| 5,167,244 A | 12/1992 | Kjerstad |
| 5,191,906 A | 3/1993 | Myracle, Jr. |
| 5,220,930 A | 6/1993 | Gentry |
| 5,225,277 A | 7/1993 | Takegawa et al. |
| 5,240,117 A | 8/1993 | Focke et al. |
| 5,271,419 A | 12/1993 | Arzonico et al. |
| 5,333,729 A | 8/1994 | Wolfe |
| 5,353,357 A | 10/1994 | Longest et al. |
| 5,360,023 A | 11/1994 | Blakeley et al. |
| 5,387,285 A | 2/1995 | Rivers |
| 5,396,909 A | 3/1995 | Gentry et al. |
| 5,432,600 A | 7/1995 | Grollimund et al. |
| 5,472,002 A | 12/1995 | Covarrubias |
| 5,476,108 A | 12/1995 | Dominguez et al. |
| 5,515,159 A | 5/1996 | Sites et al. |
| 5,588,068 A | 12/1996 | Longest et al. |
| 5,660,382 A | 8/1997 | Meier |
| 5,718,250 A | 2/1998 | Banerjee et al. |
| 5,740,902 A | 4/1998 | Spatafora |
| 5,898,104 A | 4/1999 | Rohrssen et al. |
| 5,938,018 A | 8/1999 | Keaveney et al. |
| 5,977,780 A | 11/1999 | Herrmann |
| 6,020,969 A | 2/2000 | Struckhoff et al. |
| 6,054,665 A | 4/2000 | Focke et al. |
| 6,117,455 A | 9/2000 | Takada et al. |
| 6,158,193 A | 12/2000 | Focke et al. |
| 6,213,128 B1 | 4/2001 | Smith et al. |
| 6,229,115 B1 | 5/2001 | Vos et al. |
| 6,246,778 B1 | 6/2001 | Moore |
| 6,301,380 B1 * | 10/2001 | Mullins ................... B65B 19/28 209/587 |
| 6,360,751 B1 | 3/2002 | Fagg et al. |
| 6,384,359 B1 | 5/2002 | Belcastro et al. |
| 6,385,333 B1 | 5/2002 | Puckett et al. |
| 6,437,317 B1 | 8/2002 | Focke et al. |
| 6,537,186 B1 | 3/2003 | Veluz |
| 6,612,429 B2 | 9/2003 | Dennen |
| 6,647,878 B2 | 11/2003 | Blau et al. |
| 6,694,708 B2 | 2/2004 | Brizzi et al. |
| 6,726,006 B1 | 4/2004 | Funderburk et al. |
| 6,736,261 B1 | 5/2004 | Thomas et al. |
| 6,761,174 B2 | 7/2004 | Jupe et al. |
| 6,779,530 B2 | 8/2004 | Kraker |
| 6,813,961 B2 | 11/2004 | Stiller et al. |
| 6,848,449 B2 | 2/2005 | Kitao et al. |
| 6,904,917 B2 | 6/2005 | Kitao et al. |
| 7,074,170 B2 | 7/2006 | Lanier, Jr. et al. |
| 7,115,085 B2 | 10/2006 | Deal |
| 7,210,486 B2 | 5/2007 | Hartmann |
| 7,234,271 B1 | 6/2007 | Fitzgerald et al. |
| 7,237,559 B2 | 7/2007 | Ashcraft et al. |
| 7,240,678 B2 | 7/2007 | Crooks et al. |
| 7,275,548 B2 | 10/2007 | Hancock et al. |
| 7,281,540 B2 | 10/2007 | Barnes et al. |
| 7,296,578 B2 | 11/2007 | Read, Jr. |
| 7,325,382 B2 | 2/2008 | Nelson et al. |
| 7,434,585 B2 | 10/2008 | Holmes |
| 7,479,098 B2 | 1/2009 | Thomas et al. |
| 7,565,818 B2 | 7/2009 | Thomas et al. |
| 7,578,298 B2 | 8/2009 | Karles et al. |
| 7,654,945 B2 | 2/2010 | Deal |
| 7,740,019 B2 | 6/2010 | Nelson et al. |
| 7,744,922 B2 | 6/2010 | Mane et al. |
| 7,784,356 B2 | 8/2010 | Spiers et al. |
| 7,833,146 B2 | 11/2010 | Deal |
| 7,836,895 B2 | 11/2010 | Dube et al. |
| 7,861,728 B2 | 1/2011 | Holton, Jr. et al. |
| 7,972,254 B2 | 7/2011 | Stokes et al. |
| 8,142,339 B2 | 3/2012 | Deal |
| 8,186,359 B2 | 5/2012 | Ademe et al. |
| 8,262,550 B2 | 9/2012 | Barnes et al. |
| 8,308,623 B2 | 11/2012 | Nelson et al. |
| 2001/0032932 A1 | 10/2001 | Focke |

(56) References Cited

U.S. PATENT DOCUMENTS

| | | |
|---|---|---|
| 2002/0185141 A1 | 12/2002 | Heide |
| 2003/0136419 A1 | 7/2003 | Muller |
| 2003/0137312 A1 | 7/2003 | Cerati et al. |
| 2003/0145866 A1 | 8/2003 | Hartmann |
| 2003/0178036 A1 | 9/2003 | Demmer et al. |
| 2003/0206023 A1 | 11/2003 | Herrmann |
| 2004/0129281 A1 | 7/2004 | Hancock et al. |
| 2004/0141174 A1 | 7/2004 | Focke et al. |
| 2004/0217023 A1 | 11/2004 | Fagg et al. |
| 2004/0256253 A1 | 12/2004 | Henson et al. |
| 2004/0261807 A1 | 12/2004 | Dube et al. |
| 2005/0016556 A1 | 1/2005 | Ashcraft et al. |
| 2005/0039764 A1 | 2/2005 | Barnes et al. |
| 2005/0066986 A1 | 3/2005 | Nestor et al. |
| 2005/0075754 A1 | 4/2005 | Zeitler et al. |
| 2005/0076929 A1 | 4/2005 | Fitzgerald et al. |
| 2005/0112228 A1 | 5/2005 | Smith et al. |
| 2005/0150786 A1 | 7/2005 | Mitten et al. |
| 2006/0169295 A1 | 8/2006 | Draghetti |
| 2006/0207616 A1 | 9/2006 | Hapke et al. |
| 2006/0243611 A1 | 11/2006 | Wu |
| 2006/0272655 A1 | 12/2006 | Thomas et al. |
| 2007/0056600 A1 | 3/2007 | Coleman, III et al. |
| 2007/0091326 A1 | 4/2007 | Schroeder et al. |
| 2007/0102015 A1 | 5/2007 | Villarinho |
| 2007/0144542 A1 | 6/2007 | Bencivenni et al. |
| 2007/0215167 A1 | 9/2007 | Crooks et al. |
| 2007/0246055 A1 | 10/2007 | Oglesby |
| 2008/0029118 A1 | 2/2008 | Nelson et al. |
| 2008/0093234 A1 | 4/2008 | Jones et al. |
| 2008/0099353 A1 | 5/2008 | Parsons et al. |
| 2008/0142028 A1 | 6/2008 | Fagg |
| 2008/0179204 A1 | 7/2008 | Lutzig |
| 2008/0202540 A1 | 8/2008 | Carter et al. |
| 2009/0050163 A1 | 2/2009 | Hartmann et al. |
| 2009/0066948 A1 | 3/2009 | Karpowicz et al. |
| 2009/0090372 A1 | 4/2009 | Thomas et al. |
| 2009/0120449 A1 | 5/2009 | Tindall |
| 2009/0194118 A1 | 8/2009 | Ademe et al. |
| 2010/0059074 A1 | 3/2010 | Brantley et al. |
| 2010/0101589 A1 | 4/2010 | Nelson et al. |
| 2010/0184576 A1 | 7/2010 | Prestia et al. |
| 2010/0186351 A1 | 7/2010 | Carter et al. |
| 2010/0236561 A1 | 9/2010 | Barnes et al. |
| 2010/0293106 A1 | 11/2010 | Rhoads et al. |
| 2010/0294290 A1 | 11/2010 | Zhang |
| 2011/0053745 A1 | 3/2011 | Iliev et al. |
| 2011/0067976 A1 | 3/2011 | Pelagatti |
| 2011/0162662 A1 | 7/2011 | Nikolov et al. |
| 2011/0162665 A1 | 7/2011 | Burov et al. |
| 2011/0169942 A1 | 7/2011 | Brantley et al. |
| 2011/0230320 A1 | 9/2011 | Stokes et al. |
| 2011/0271968 A1 | 11/2011 | Carpenter et al. |
| 2012/0037546 A1 | 2/2012 | Dixon et al. |
| 2012/0055493 A1 | 3/2012 | Novak, III et al. |
| 2012/0077658 A1 | 3/2012 | Nikolov et al. |
| 2012/0080043 A1 | 4/2012 | Naenen et al. |
| 2012/0120229 A1* | 5/2012 | Brantley ............ B65B 19/28 348/92 |
| 2012/0245006 A1 | 9/2012 | Henley et al. |
| 2012/0245007 A1 | 9/2012 | Henley et al. |
| 2013/0085052 A1 | 4/2013 | Novak, III et al. |
| 2013/0096711 A1 | 4/2013 | Gates et al. |
| 2014/0290180 A1* | 10/2014 | Olbrich ............. B65B 19/28 53/411 |

FOREIGN PATENT DOCUMENTS

| | | |
|---|---|---|
| CN | 1642724 | 7/2005 |
| CN | 1939165 | 4/2007 |
| CN | 101257809 | 9/2008 |
| DE | 10238906 | 3/2004 |
| DE | 10 2006 058 370 | 6/2008 |
| DE | 10 2008 062 370 | 6/2010 |
| EP | 0 292 949 | 11/1988 |
| EP | 0 704 172 | 4/1996 |
| EP | 0 902 275 | 3/1999 |
| EP | 1 669 755 | 6/2006 |
| EP | 1 754 419 | 2/2007 |
| EP | 1 767 107 | 3/2007 |
| EP | 1 916 188 | 4/2008 |
| EP | 2 243 384 | 10/2010 |
| GB | 1 058 343 | 2/1967 |
| GB | 2 020 158 | 11/1979 |
| GB | 1042000 | 9/1996 |
| JP | 9325123 | 12/1997 |
| JP | 2001-190262 | 7/2001 |
| JP | 2003-219855 | 8/2003 |
| JP | 2004-504825 | 2/2004 |
| WO | WO 00/22826 | 4/2000 |
| WO | WO 01/79092 | 10/2001 |
| WO | WO 03/009711 | 2/2003 |
| WO | WO 03/047836 | 6/2003 |
| WO | WO 03/082558 | 10/2003 |
| WO | WO 2005/113386 | 12/2005 |
| WO | WO 2006/064371 | 6/2006 |
| WO | WO 2006/092962 | 9/2006 |
| WO | WO 2007/028957 | 3/2007 |
| WO | WO 2007/038053 | 4/2007 |
| WO | WO 2013/093893 | 6/2013 |
| WO | WO 2013/145163 | 10/2013 |

OTHER PUBLICATIONS

Davis et al., *Tobacco Production, Chemistry and Technology*, 1999, pp. 440-460, Blackwell Science, Inc., Malden, MA.

Johnson, *Development of Cigarette Components to Meet Industry Needs*, $52^{nd}$ T.S.R.C., Sep. 1998.

mini-Z™ Terahertz Time Domain Spectrometer Brochure http://dl.z-thz.com/brochures/mini-ZRev5.pdf downloaded from website on Jan. 16, 2013.

\* cited by examiner

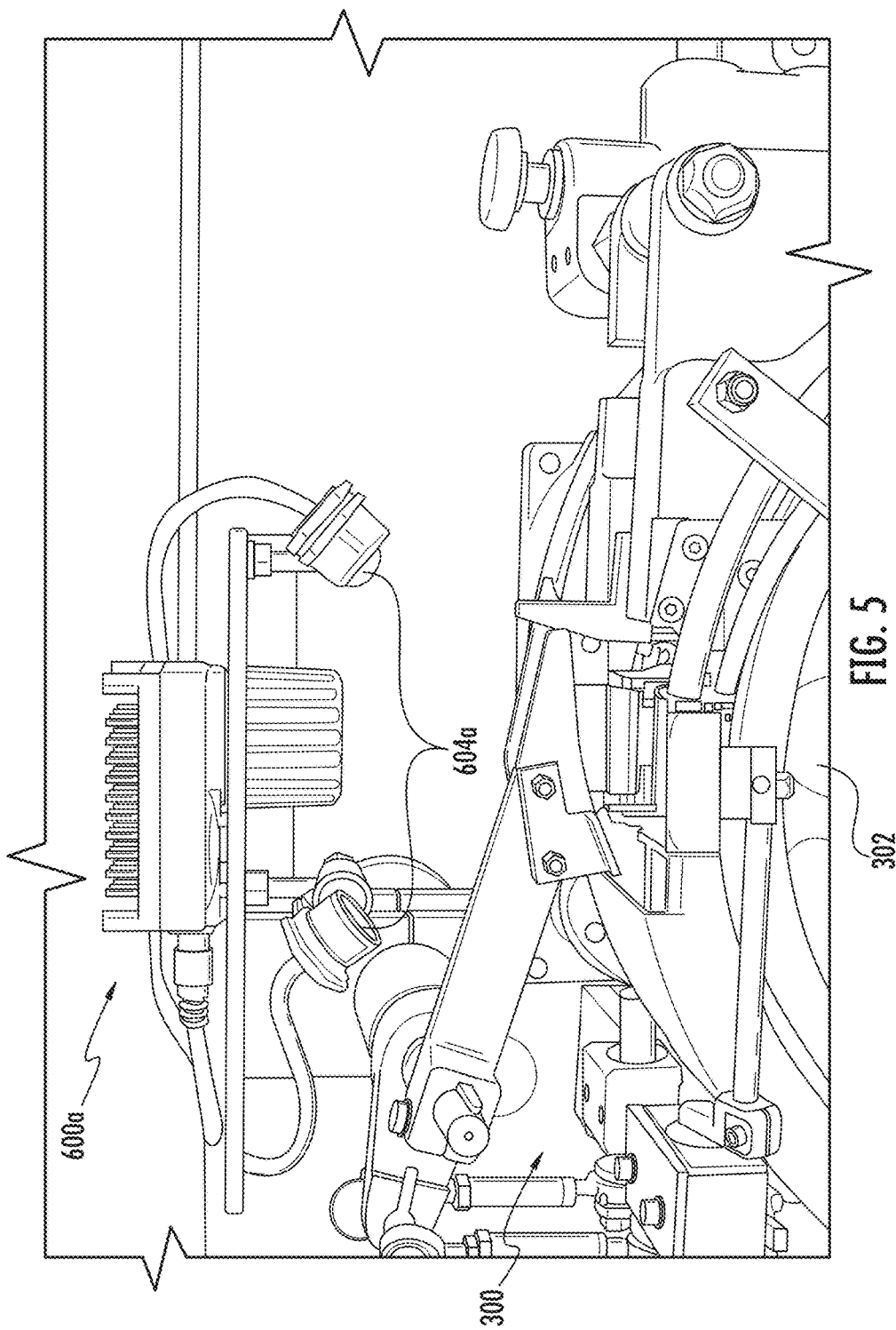

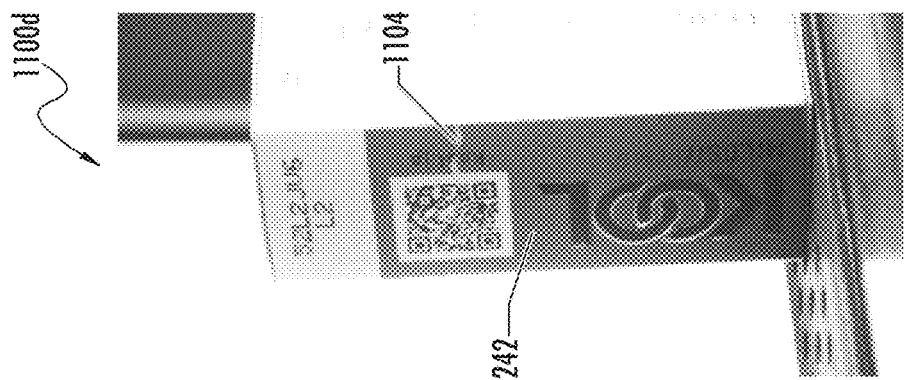
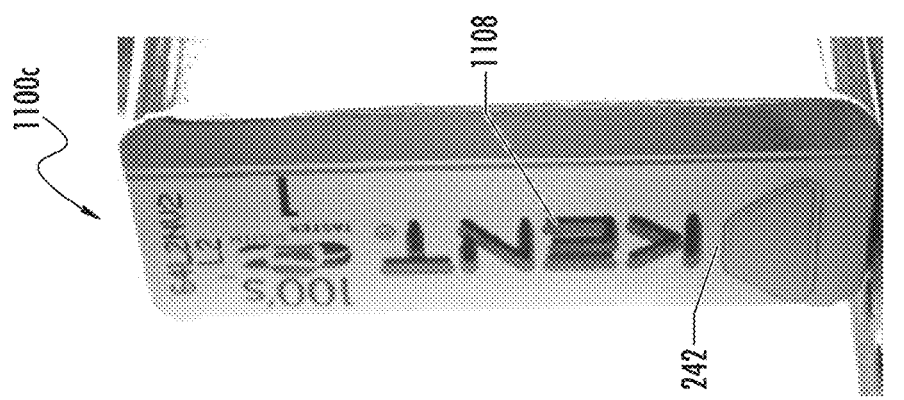
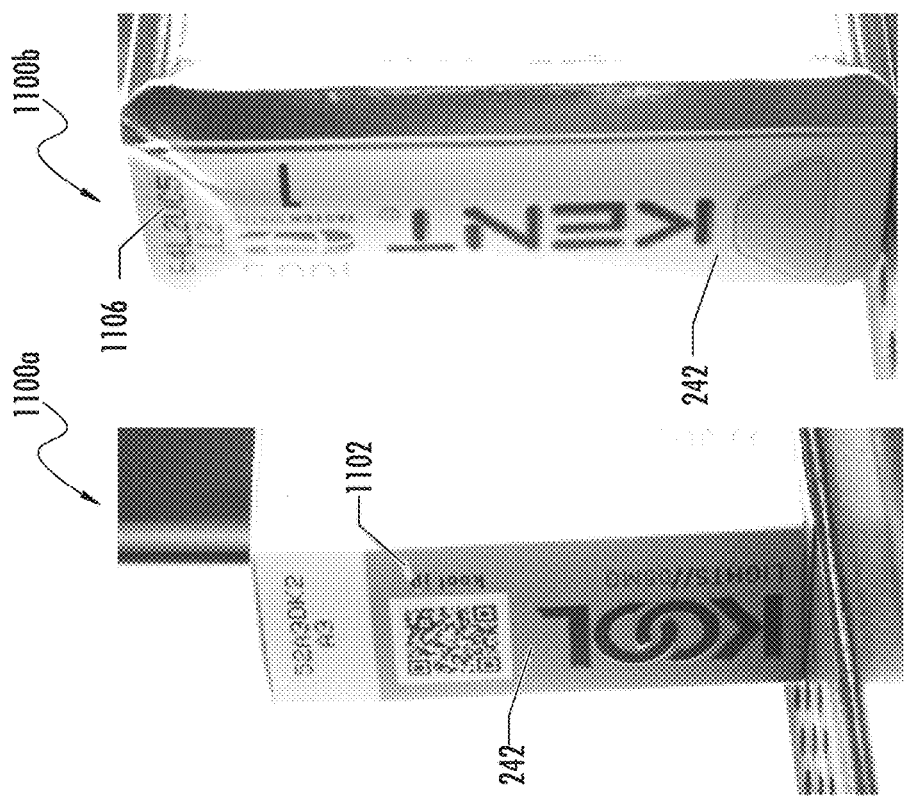
FIG. 17A  FIG. 17B  FIG. 17C  FIG. 17D

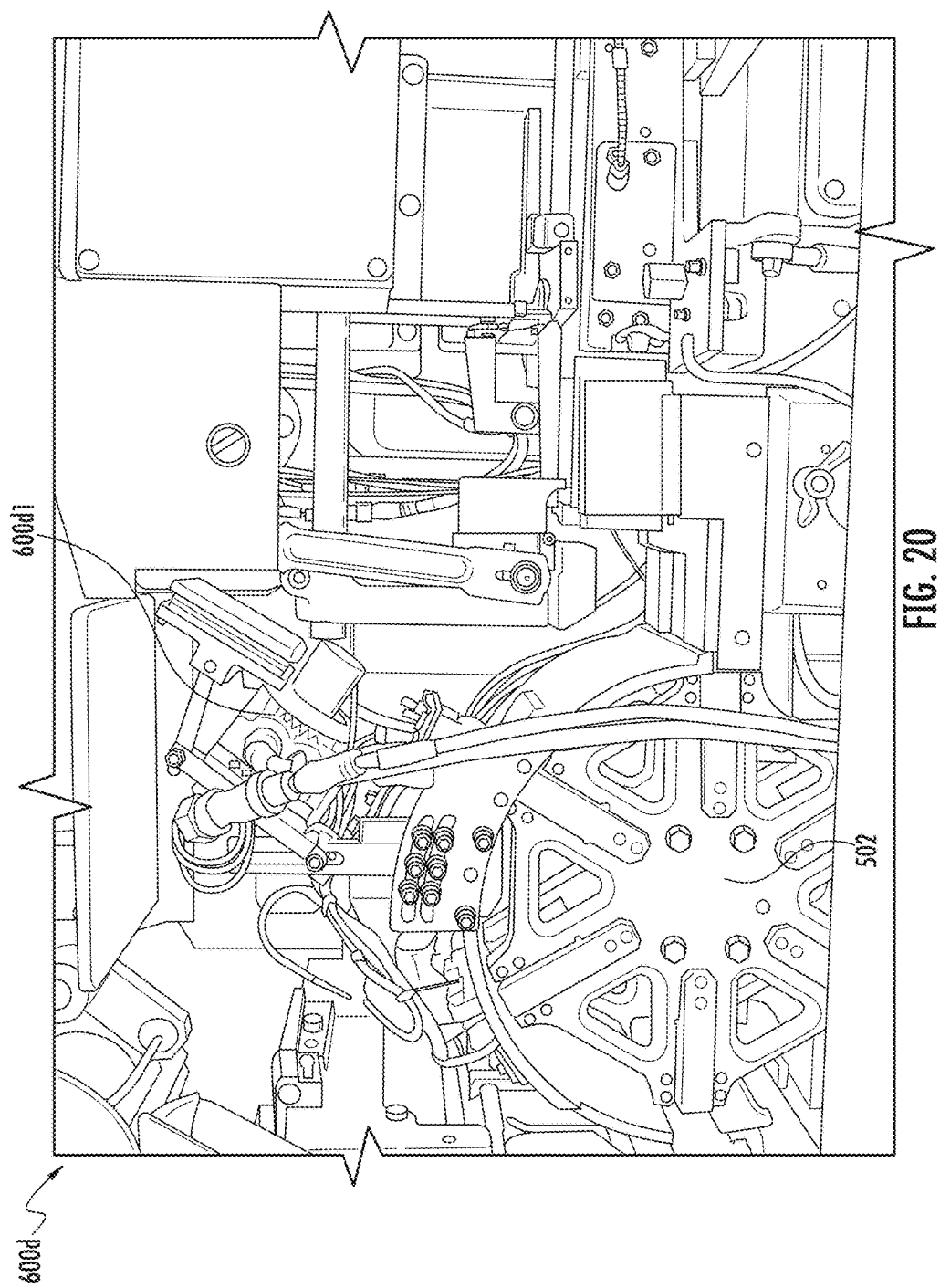

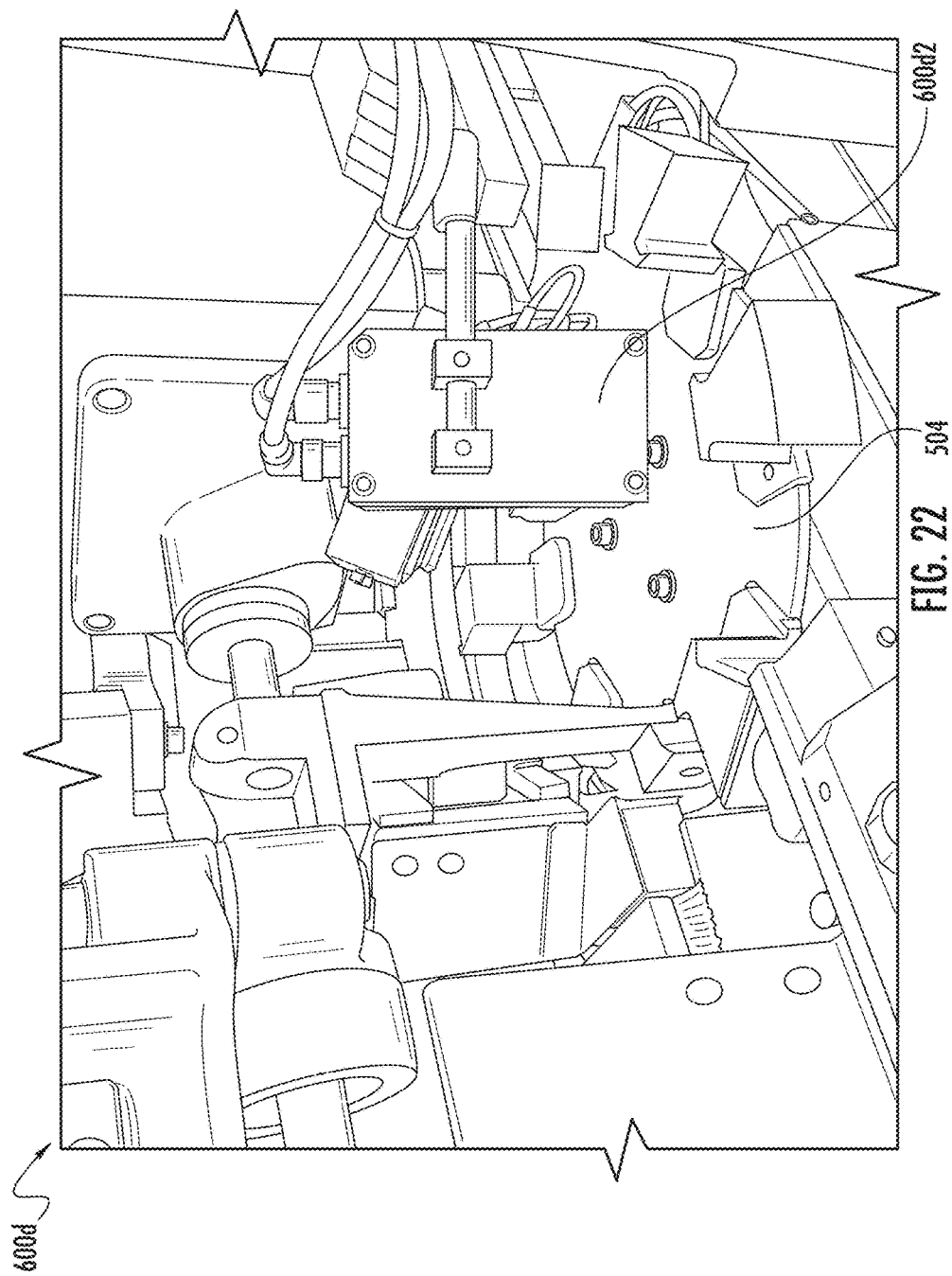

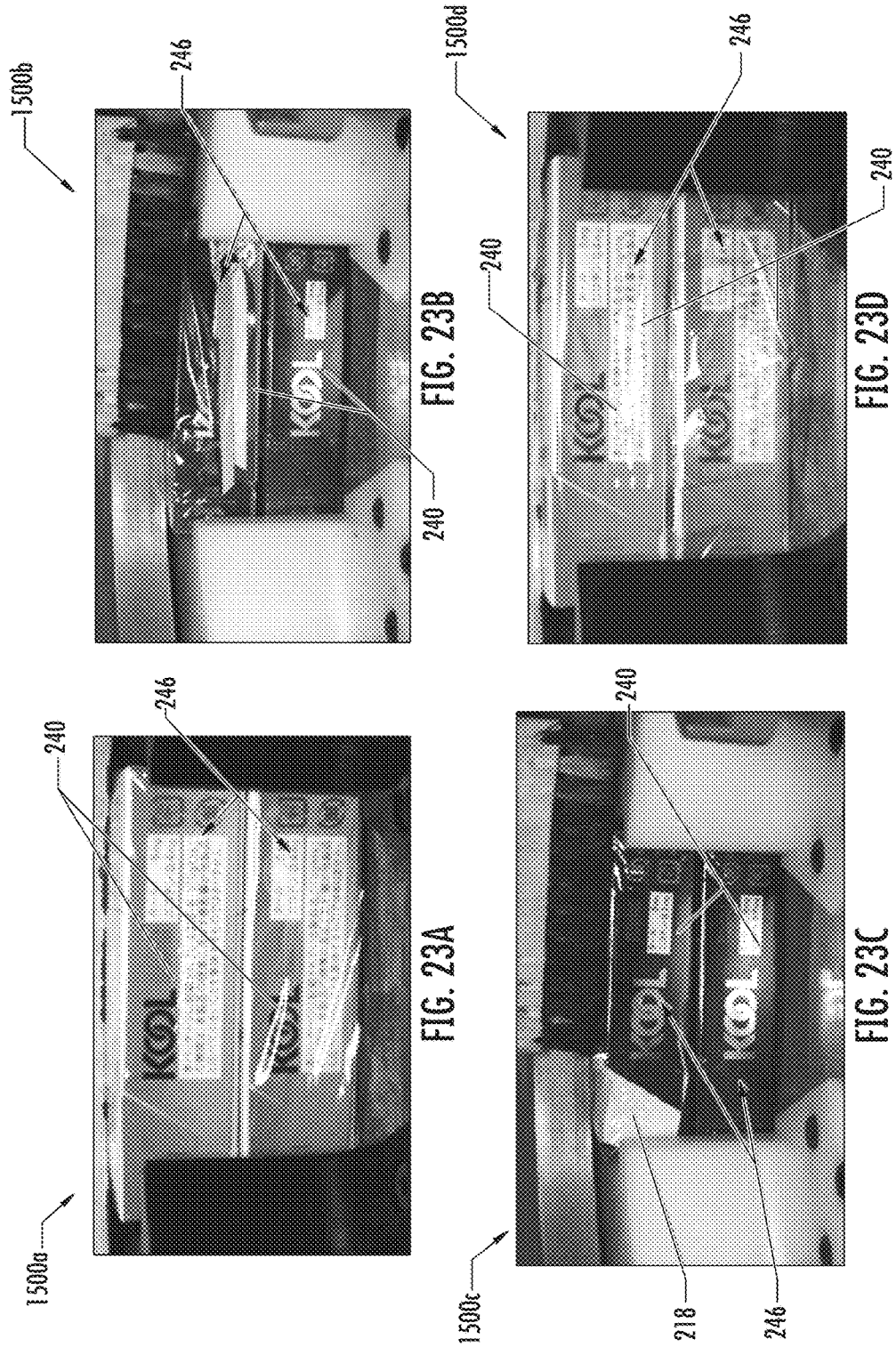

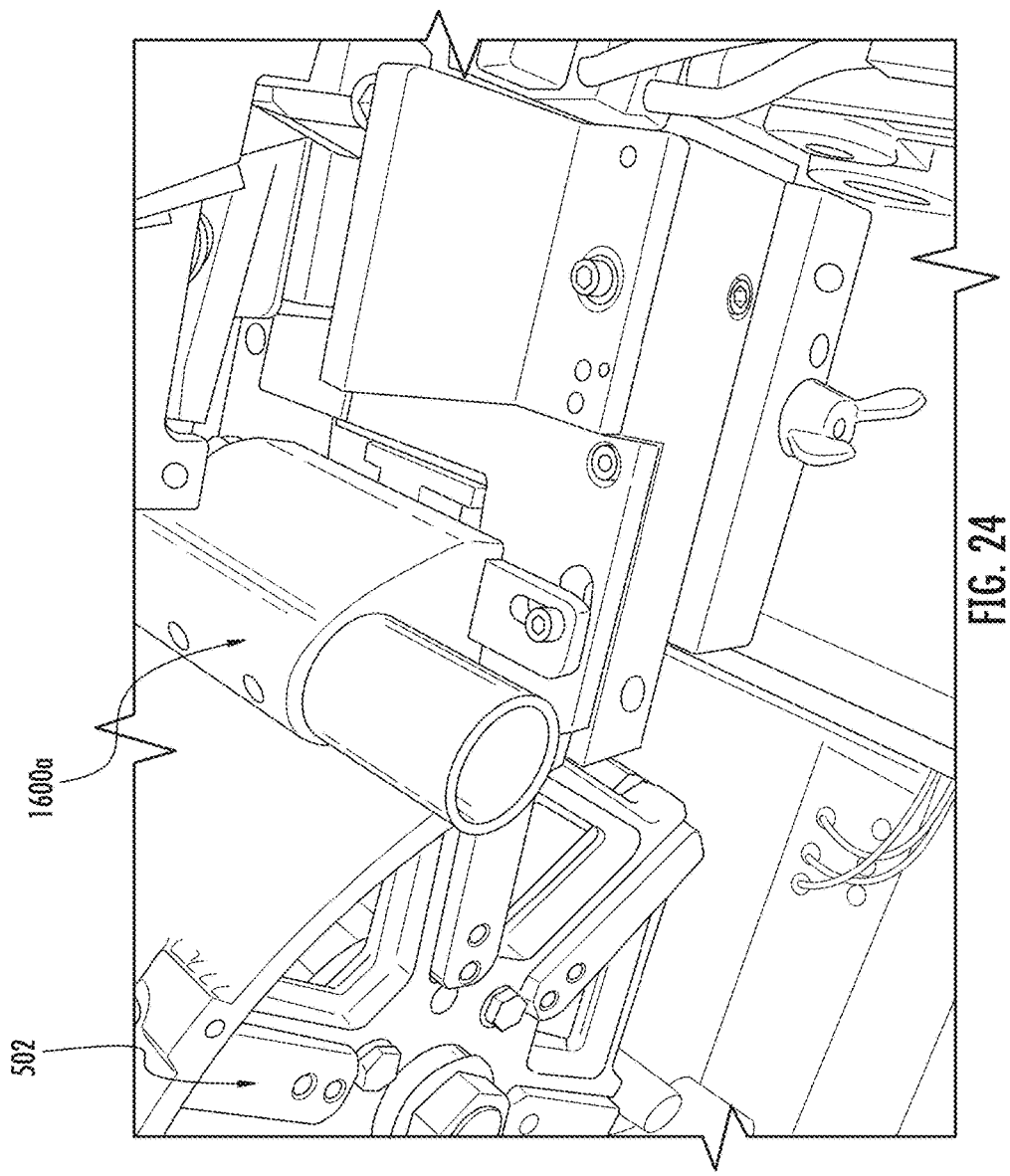

SMOKING ARTICLE PACKAGE INSPECTION SYSTEM AND ASSOCIATED METHOD

FIELD OF THE DISCLOSURE

The present disclosure relates to smoking articles and more particularly to a smoking article package inspection system and a related method. The smoking articles may be made or derived from tobacco, or otherwise incorporate tobacco, and may be intended for human consumption.

BACKGROUND OF THE DISCLOSURE

Popular smoking articles, such as cigarettes, typically have a substantially cylindrical rod shaped structure and include a charge, roll, or column of smokable material such as shredded tobacco (e.g., in cut filler form) surrounded by a paper wrapper thereby forming a so-called "smokable rod" or "tobacco rod." Normally, a cigarette has a cylindrical filter element aligned in an end-to-end relationship with the tobacco rod. Typically, a filter element comprises cellulose acetate tow plasticized using a plasticizer such as triacetin, and the tow is circumscribed by a paper material known as "plug wrap."

The filter element may be attached to one end of the tobacco rod using a circumscribing wrapping material known as "tipping paper," in order to provide a so-called "filtered cigarette." More particularly, the filter element may be attached to the tobacco rod using tipping material (e.g., essentially air impermeable tipping paper), that circumscribes at least a portion of both the filter element and the tobacco rod. The inner surface of the tipping material may be fixedly secured to the outer surface of the plug wrap circumscribing the filter tow and the outer surface of the wrapping material/paper wrapper surrounding the smokable material of the tobacco rod, using a suitable adhesive. Accordingly, the filter element and the tobacco rod are connected to one another. The adhesive may also function to secure the overlapping ends of the tipping material circumscribing the filter element and tobacco rod. The tipping material and plug wrap may be perforated in order to provide dilution of drawn mainstream smoke with ambient air.

In any instance, as-formed cigarettes may be typically provided to a cigarette packaging apparatus, where the as-formed cigarettes are loaded into a package or otherwise suitable container. Thus, the cigarettes may be packaged into cigarette packages in an automated manner. However, during automated packaging of cigarettes, certain defects may occur. It follows that, due to the high speed nature of the cigarette packaging process, many of the defects that may occur may not be readily apparent or otherwise detected before the completed cigarette package is offered for sale. As such, defects may not be discovered until a retailer receives the cigarette package or a consumer purchases the cigarette package. Such a situation is generally undesirable to the perception of the quality of the product, regardless of the actual quality of the cigarettes packaged therein. As such, there exists a need for an apparatus and method for inspecting smoking article packages configured to hold smoking articles, such as filtered cigarettes, in order to identify any defects prior to the products being distributed or sold. It may also be desirable for such a solution to be readily implemented with respect to existing cigarette packaging machinery.

SUMMARY OF THE DISCLOSURE

The above and other needs are met by aspects of the present disclosure which, in one aspect, provides a smoking article package inspection system configured to inspect a smoking article package. The smoking article package inspection system may comprise a plurality of imaging devices configured to capture a plurality of images of the smoking article package before and after one or more operations are performed thereon. The operations may include enclosing a plurality of smoking articles in the smoking article package, printing an identifier on the smoking article package, and wrapping the smoking article package with an outer wrapper. Further, the smoking article packaging system may include an analysis unit configured to analyze the images captured by the imaging devices, to determine whether the smoking article package is defective from the images thereof, and, if the smoking article package is determined to be defective, to determine one of the operations causing damage to the smoking article package from analysis of the images of the smoking article package captured before and after each of the operations.

In some embodiments at least one of the imaging devices may be positioned at or downstream of a packing unit configured to pack the smoking articles in the smoking article package, and the analysis unit may be configured to analyze the images captured by the at least one of the imaging devices at or downstream of the packing unit. At least one of the imaging devices may be positioned at the packing unit and the analysis unit may be configured to determine, at the packing unit, at least one of: whether the smoking article package is missing an inner frame, whether the inner frame is misaligned, whether the smoking article package is missing an insert, whether the insert is misaligned, and whether an inner wrapper surrounding the smoking articles is damaged. At least one of the imaging devices may be positioned downstream of the packing unit and the analysis unit may be configured to determine, downstream of the packing unit, at least one of: whether a flap of the smoking article package is open, whether a lid of the smoking article package is open, whether an ear of the smoking article package is open, whether the identifier is illegible, whether the identifier is missing print, whether the identifier is misaligned, whether the identifier is of poor quality, whether the identifier includes incorrect information, whether the smoking article package is damaged, whether the smoking article package is contaminated, and whether the smoking article package is improperly positioned.

In some embodiments at least one of the imaging devices may be positioned at or downstream of a printing unit configured to print the identifier, and the analysis unit may be configured to analyze the images captured at or downstream of the printing unit. The analysis unit may be configured to determine at least one of: whether the identifier is illegible, whether the identifier is missing print, whether the identifier is misaligned, whether the identifier is of poor quality, and whether the identifier includes incorrect information.

In some embodiments at least one of the imaging devices may be positioned at or downstream of a wrapping unit configured to wrap the smoking article package with an outer wrapper, and the analysis unit may be configured to analyze the images captured at or downstream of the wrapping unit. The analysis unit may be configured to determine at least one of: whether the outer wrapper is wrinkled, whether the smoking article package is damaged, whether the smoking article package is contaminated, and whether the smoking article package is open.

In some embodiments the smoking article inspection system may further comprise one or more strobe lights. The strobe lights may be configured to illuminate the smoking article package at the imaging devices. Further, the smoking article inspection system may be provided in combination with a smoking article packaging system configured to package a plurality of smoking articles. The smoking article packaging system may be configured to stop packaging the smoking articles when the analysis unit detects a predefined consecutive number of defective smoking article packages.

The smoking article inspection system may further comprise one or more rejecting units configured to reject the smoking article package if the analysis unit determines that the smoking article package is defective. The rejecting units may include: a rejecting unit positioned at or downstream of a packing unit configured to pack the smoking articles in the smoking article package and upstream of a printing unit configured to print the identifier, a rejecting unit positioned at or downstream of the printing unit and upstream of a wrapping unit configured to wrap the smoking article package with the outer wrapper, and a rejecting unit positioned at or downstream of the wrapping unit. The analysis unit may be configured to compare the images captured by the imaging devices to one of a plurality of stored images of defective smoking article packages and a plurality of stored images of non-defective smoking article packages to determine whether the smoking article package is defective.

In an additional aspect, a method for inspecting a smoking article package is provided. The method may include capturing a plurality of images of the smoking article package before and after one or more operations are performed thereon. The operations may include enclosing a plurality of smoking articles in the smoking article package, printing an identifier on the smoking article package, and wrapping the smoking article package with an outer wrapper. Additionally, the method may include analyzing the images to determine whether the smoking article package is defective. Further, the method may include determining one of the operations causing damage to the smoking article package from analysis of the images of the smoking article package captured before and after each of the operations, if the smoking article package is determined to be defective.

In some embodiments capturing the images of the smoking article package may include capturing the images of the smoking article package at or downstream of a packing unit configured to pack a plurality of smoking articles in the smoking article package. Capturing the images of the smoking article package may include capturing the images of the smoking article package at the packing unit. Analyzing the images may include determining, at the packing unit, at least one of: whether the smoking article package is missing an inner frame, whether the inner frame is misaligned, whether the smoking article package is missing an insert, whether the insert is misaligned, and whether an inner wrapper surrounding the smoking articles is damaged.

In some embodiments capturing the images of the smoking article package may include capturing the images of the smoking article package downstream of the packing unit. Analyzing the images may include determining, downstream of the packing unit, at least one of: whether a flap of the smoking article package is open, whether a lid of the smoking article package is open, whether an ear of the smoking article package is open, whether the identifier is illegible, whether the identifier is missing print, whether the identifier is misaligned, whether the identifier is of poor quality, whether the identifier includes incorrect information, whether the smoking article package is damaged, whether the smoking article package is contaminated, and whether the smoking article package is improperly positioned.

In some embodiments capturing the images of the smoking article package may include capturing the images of the smoking article package at or downstream of a printing unit configured to print the identifier. Analyzing the images may include determining at least one of: whether the identifier is illegible, whether the identifier is missing print, whether the identifier is misaligned, whether the identifier is of poor quality, and whether the identifier includes incorrect information.

In some embodiments capturing the images of the smoking article package may include capturing the images of the smoking article package at or downstream of a wrapping unit configured to wrap the smoking article package with an outer wrapper. Analyzing the images may include determining at least one of: whether the outer wrapper is wrinkled, whether the smoking article package is damaged, whether the smoking article package is contaminated, and whether the smoking article package is open.

In some embodiments the method may additionally include illuminating the smoking article package while capturing the images of the smoking article package. Further, the method may include packaging a plurality of smoking articles with a smoking article packaging system, and the smoking article packaging system may be configured to stop packaging the smoking articles when a predefined consecutive number of defective smoking article packages are detected. Additionally, the method may include rejecting the smoking article package when the smoking article package is determined to be defective. Rejecting the smoking article package when the smoking article package is determined to be defective may include rejecting the smoking article package upstream of a printing unit configured to print the identifier when the smoking article package is determined to be defective upstream of the printing unit, rejecting the smoking article package upstream of a wrapping unit configured to wrap the smoking article package with the outer wrapper when the smoking article package is determined to be defective upstream of the wrapping unit, and rejecting the smoking article package downstream of the wrapping unit when the smoking article package is determined to be defective at or downstream of the wrapping unit. Further, analyzing the images to determine whether the smoking article package is defective may include comparing the images captured by the imaging devices to one of a plurality of stored images of defective smoking article packages and a plurality of stored images of non-defective smoking article packages.

Aspects of the present disclosure thus address the above needs and provide these and other advantages as otherwise detailed herein.

BRIEF DESCRIPTION OF THE DRAWINGS

Figure 1:
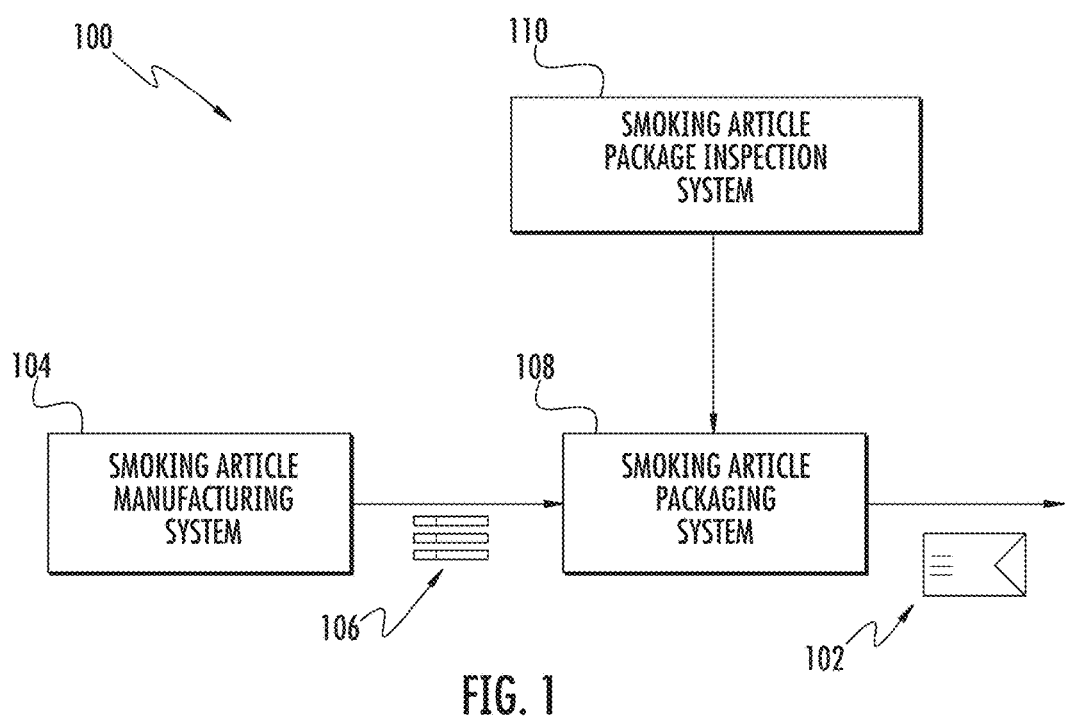
Figure 2:
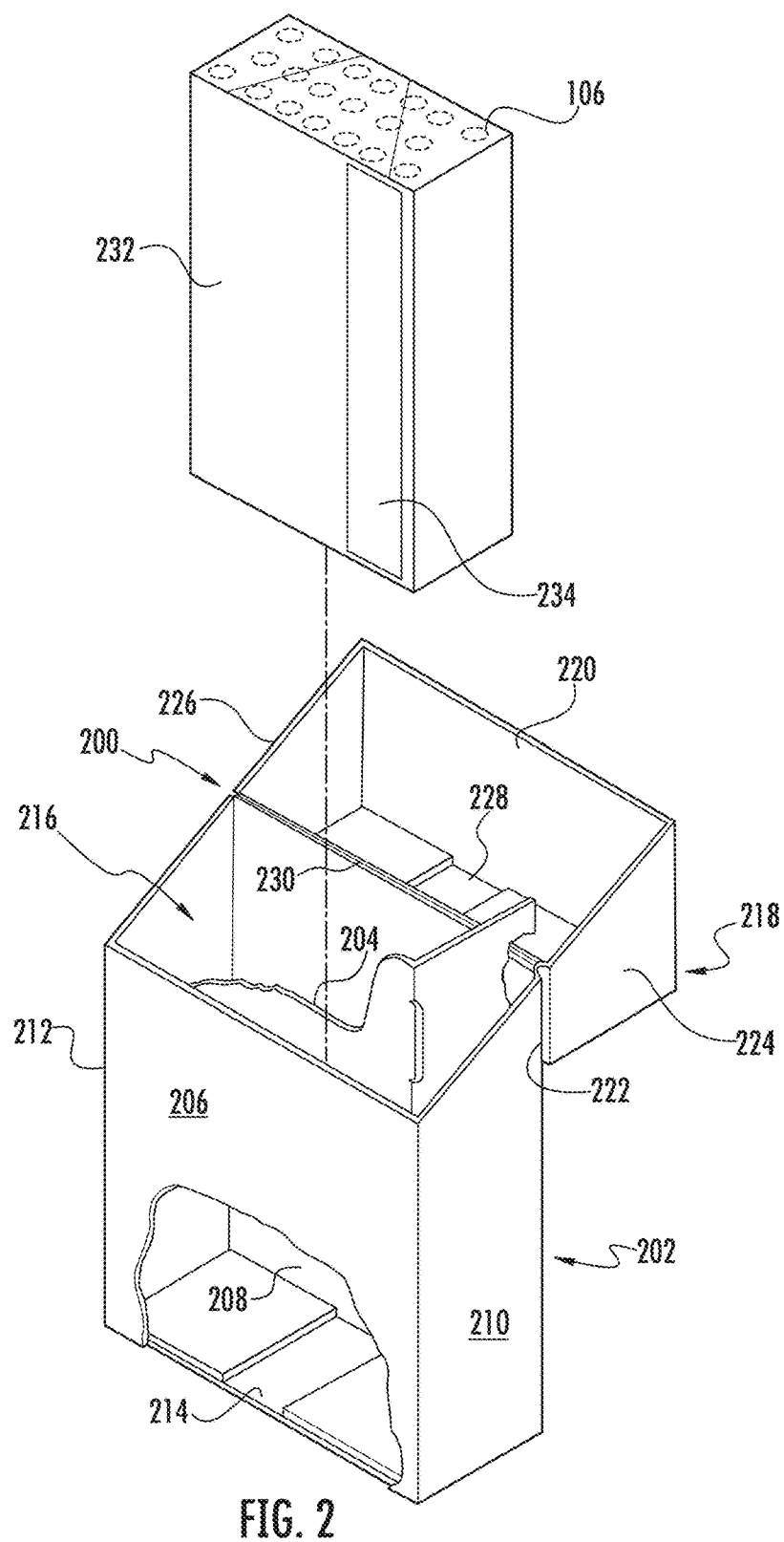
Figure 3:
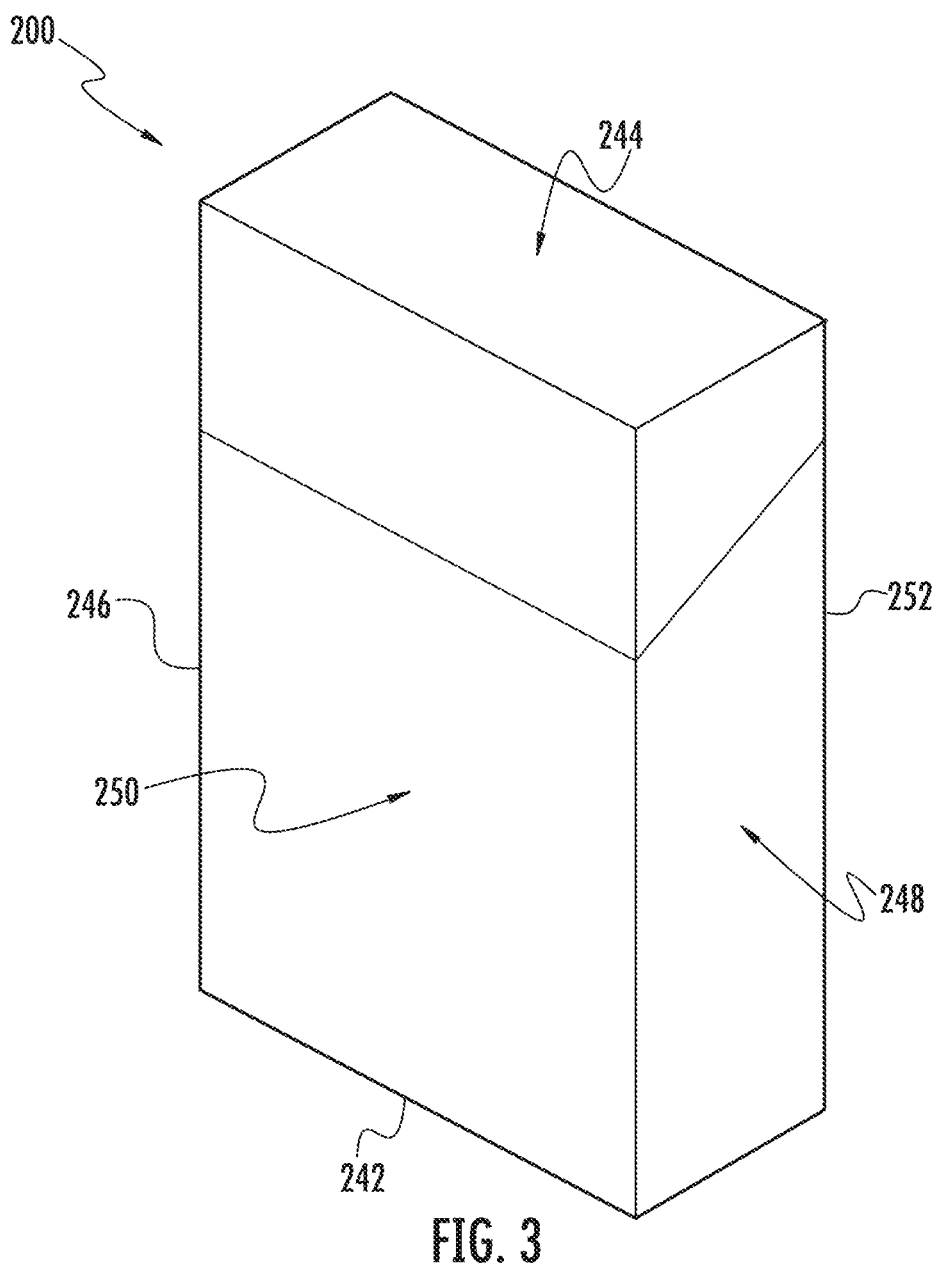
Figure 4:
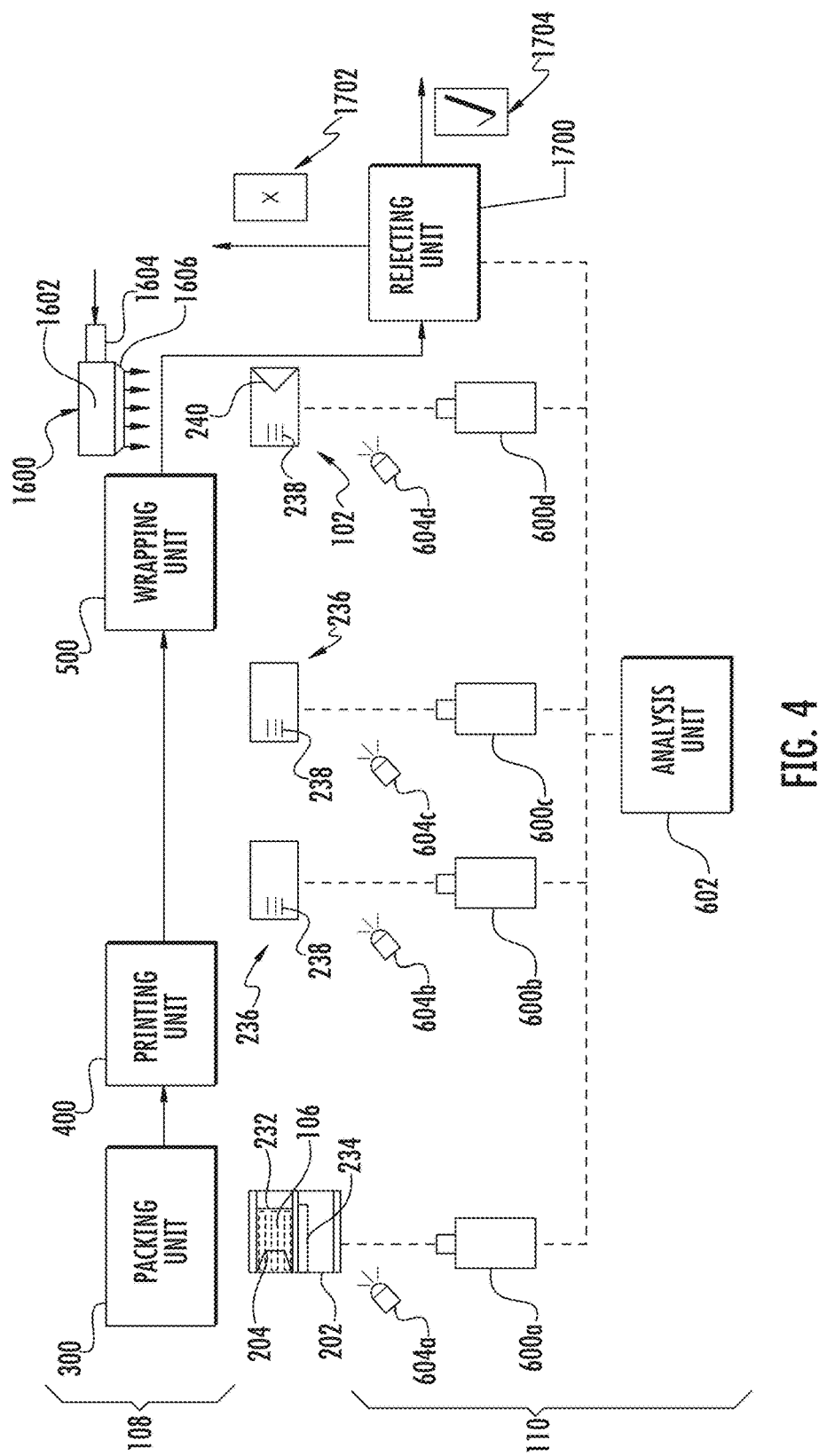
Figure 7:
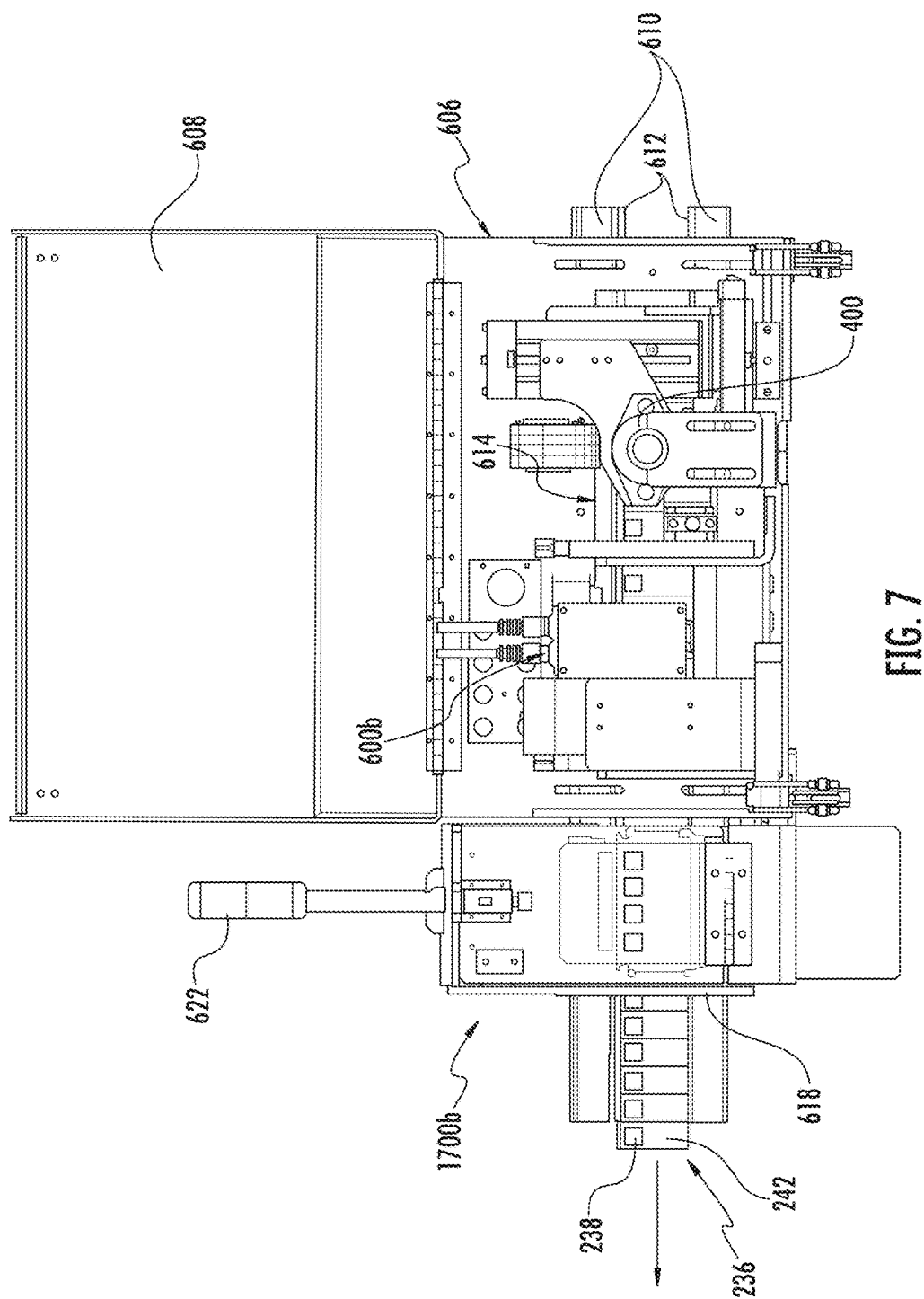
Figure 8:
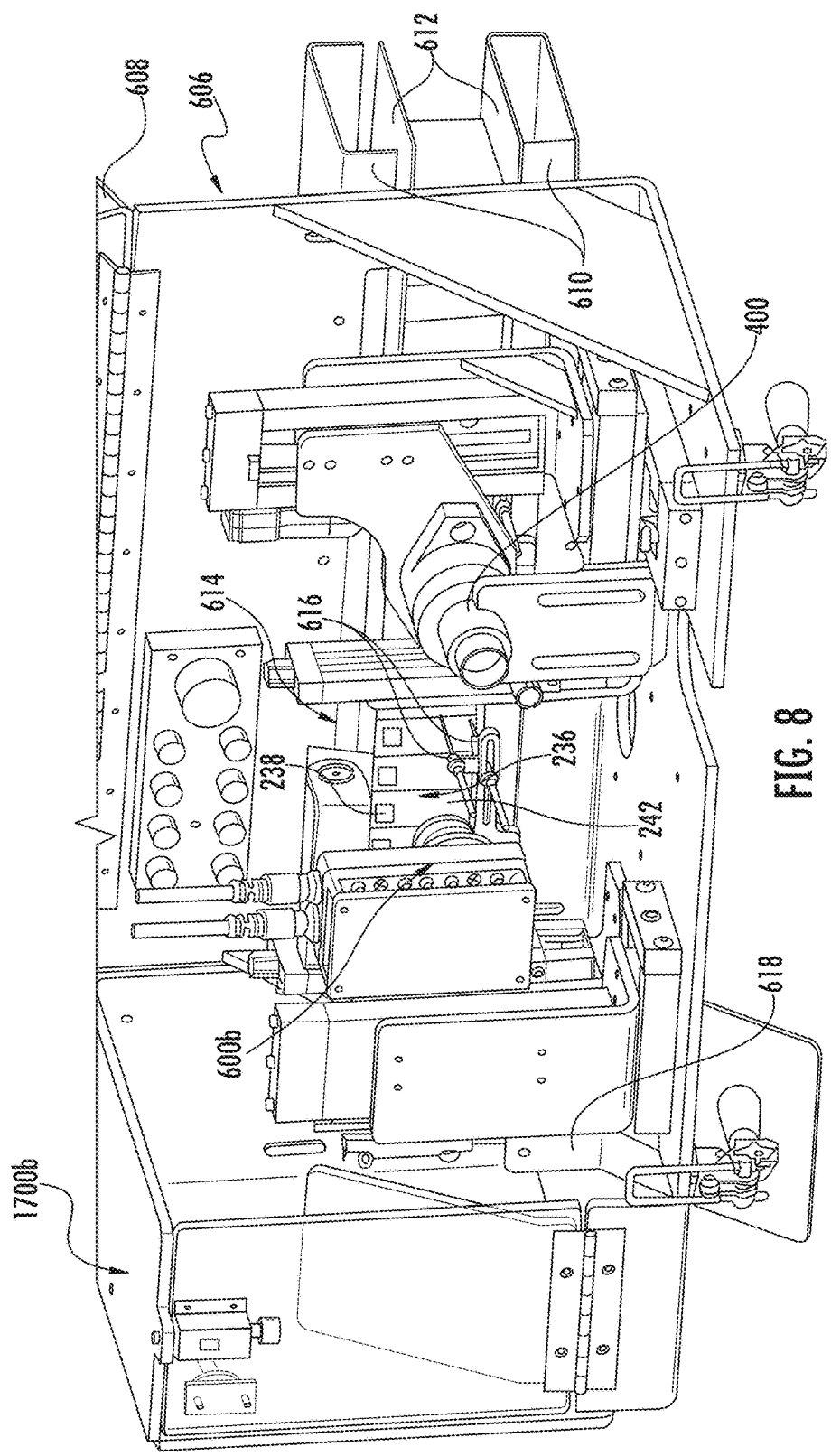
Figure 9:
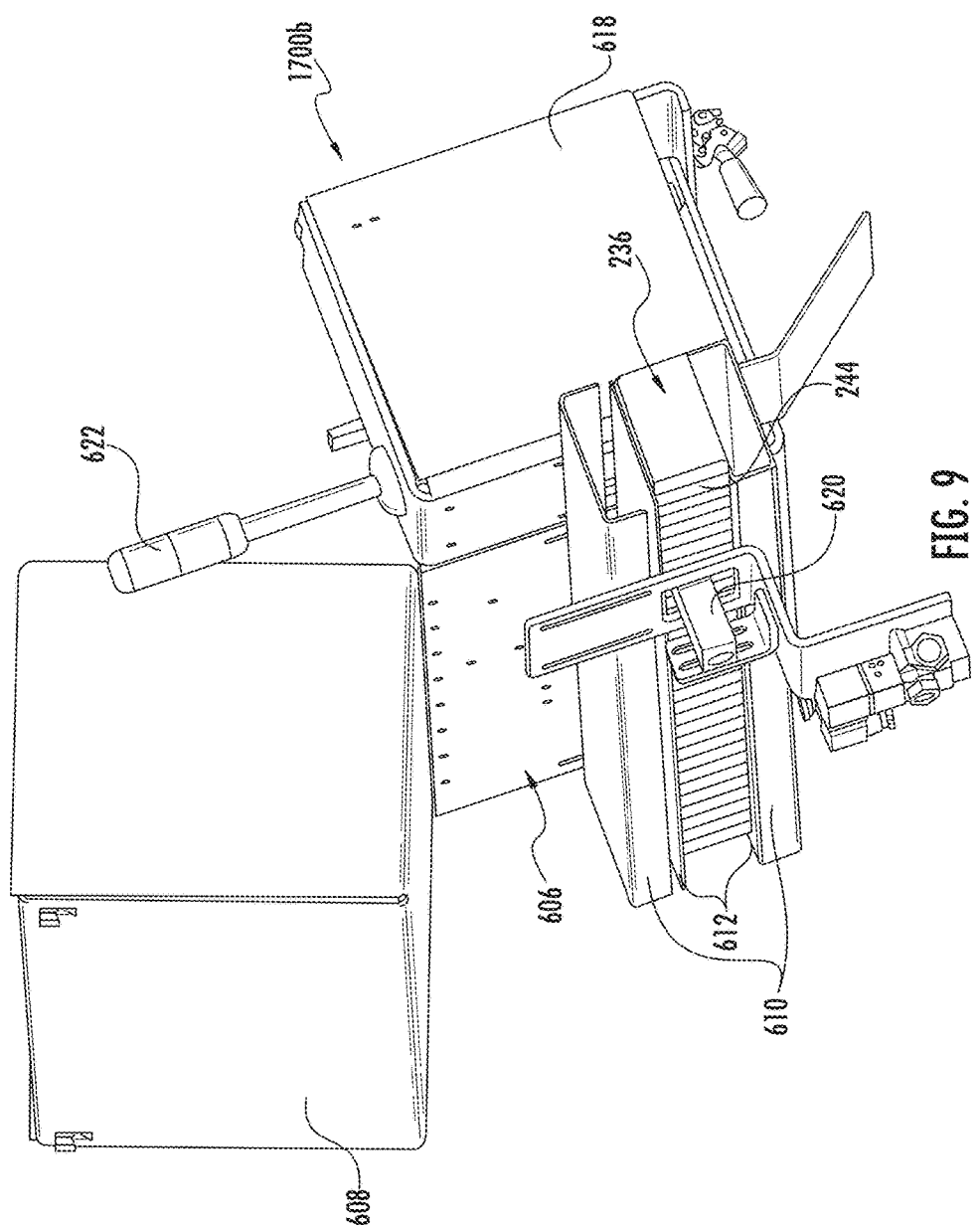
Figure 11:
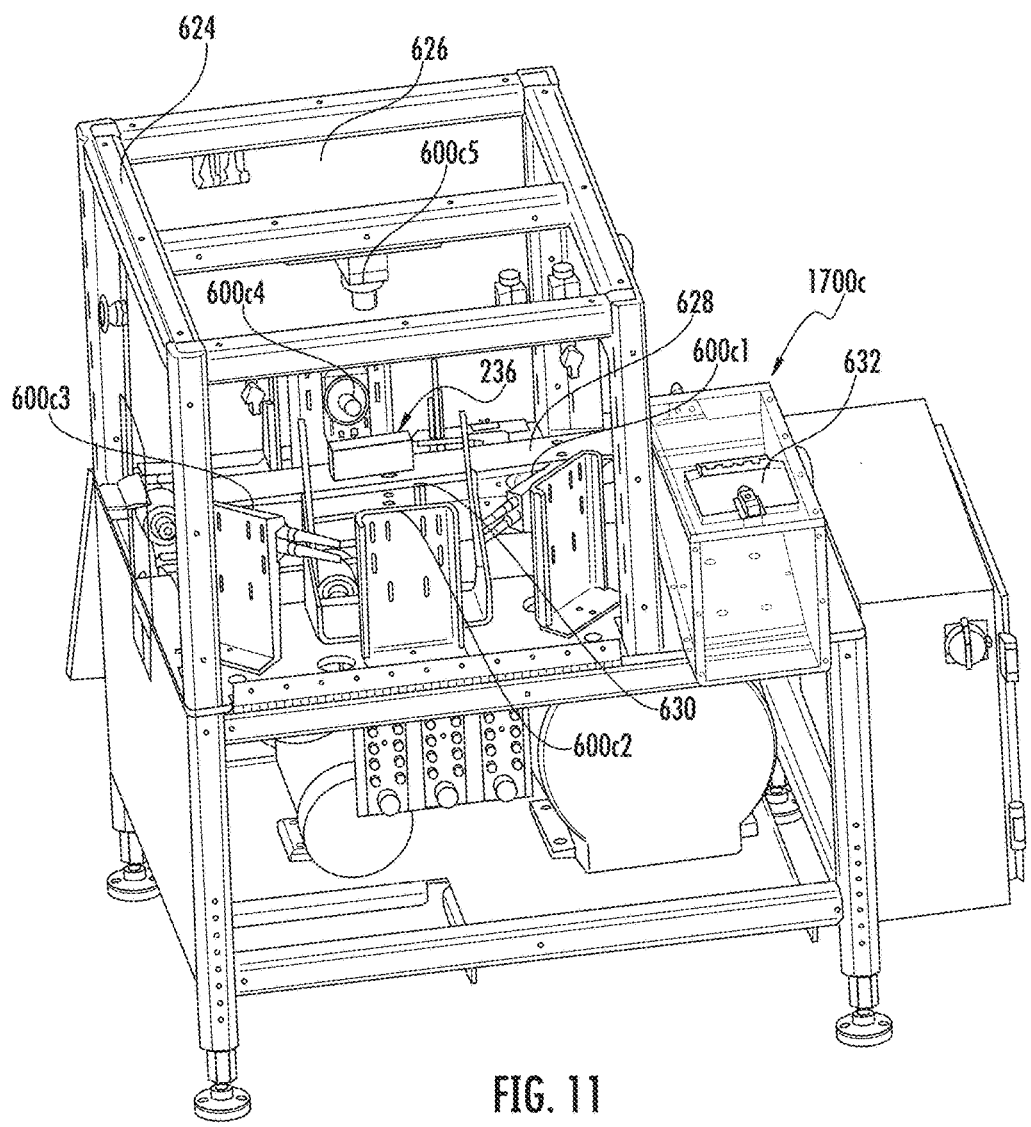
Figure 12:
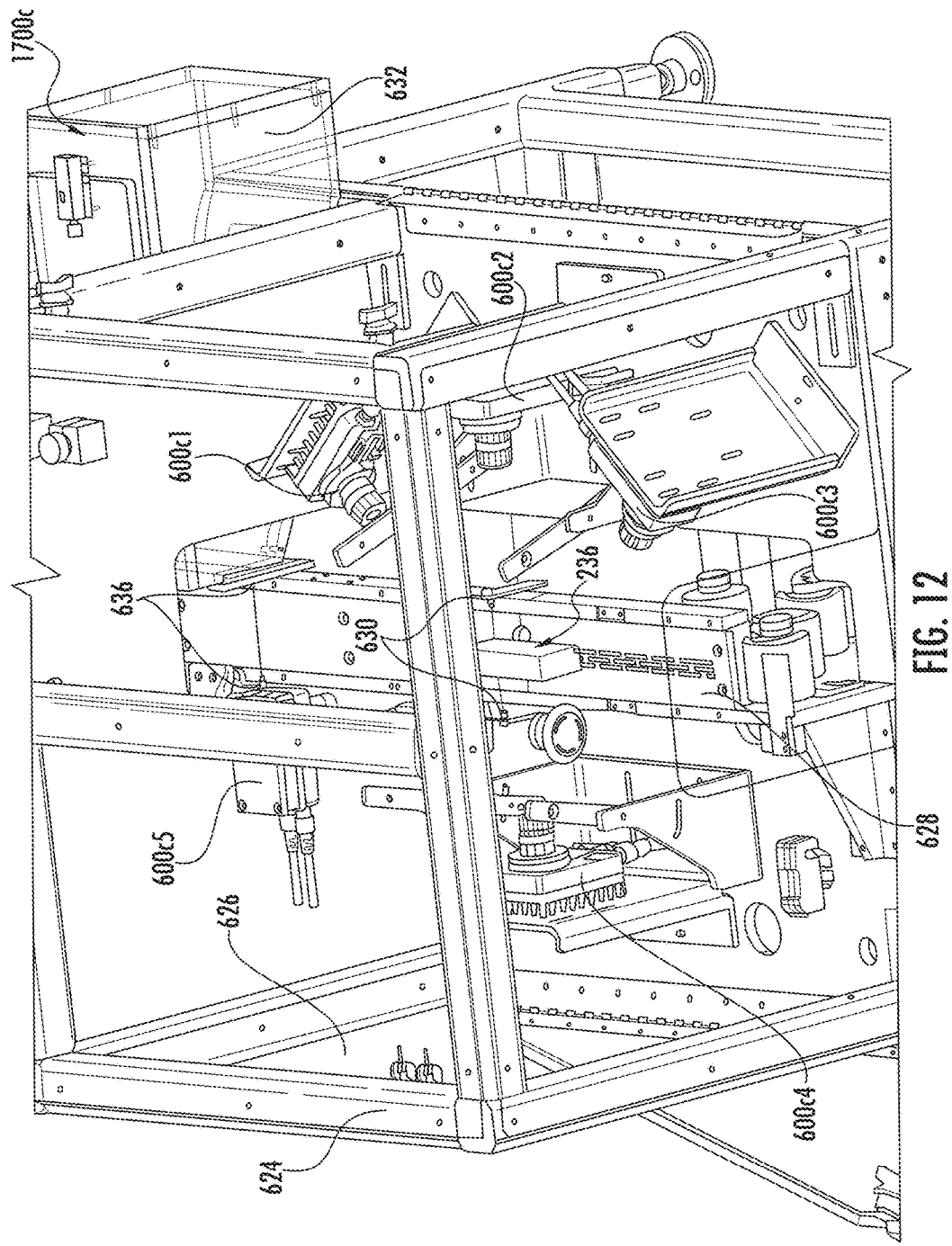
Figure 13:
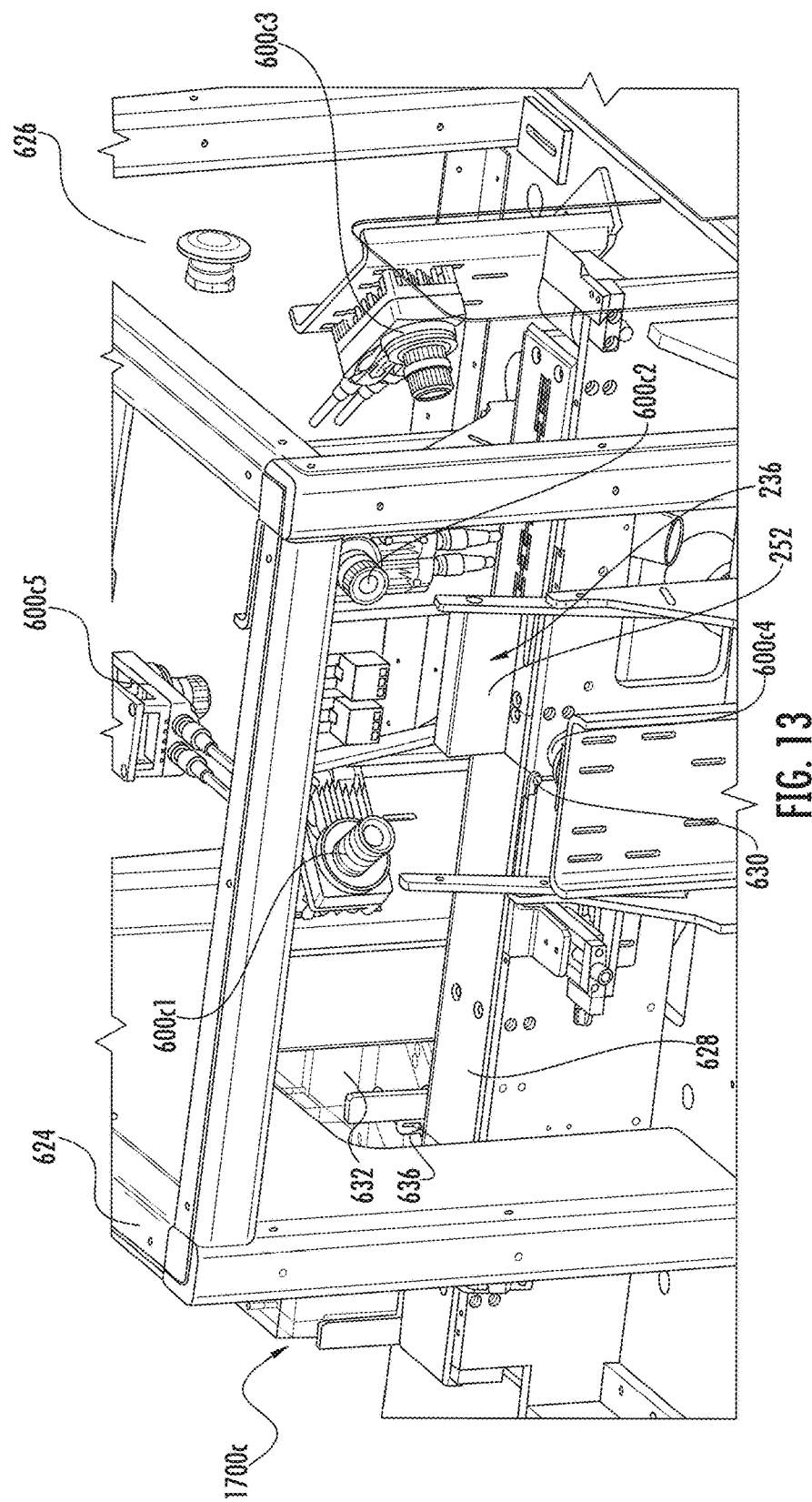
Figure 14:
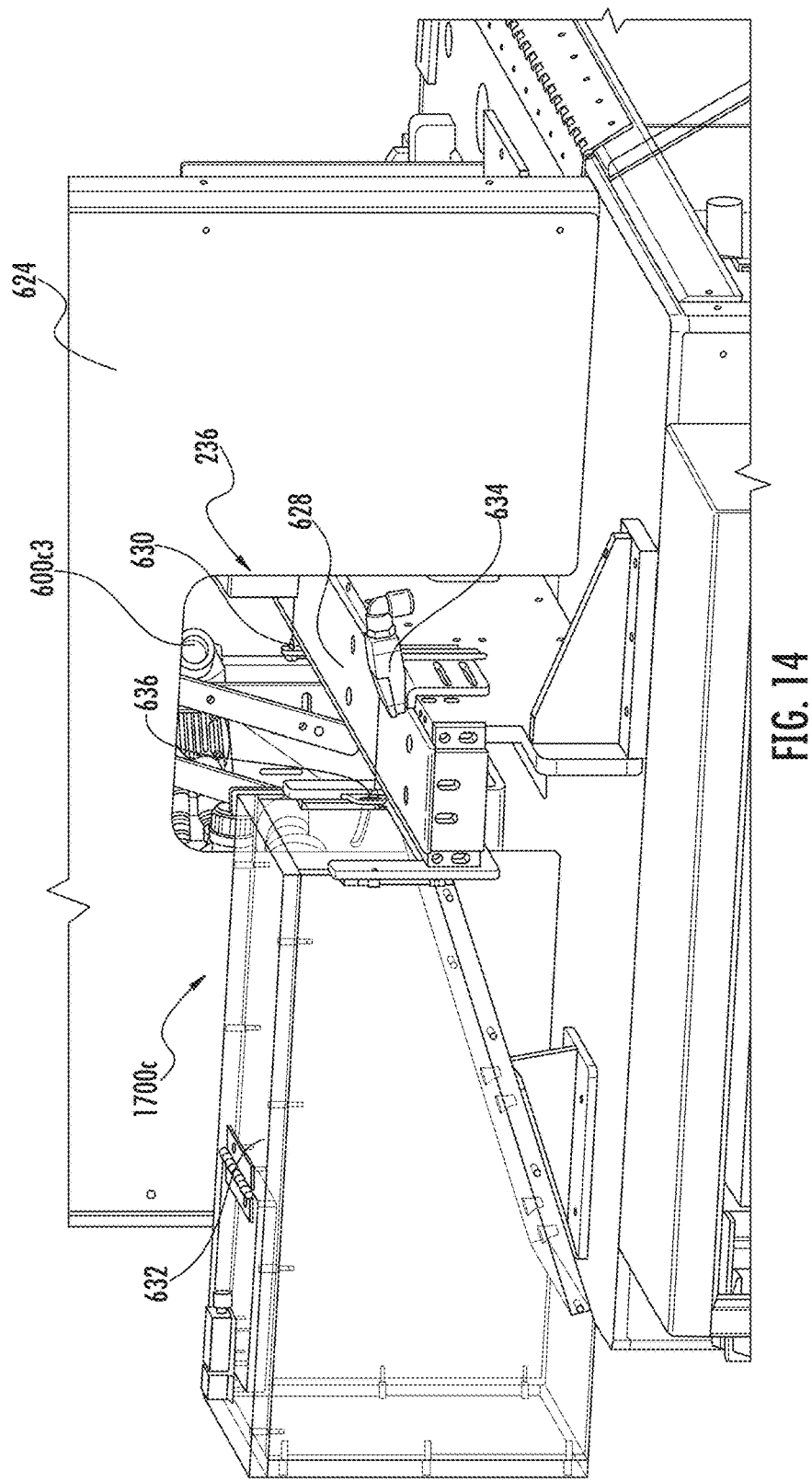
Figure 25:
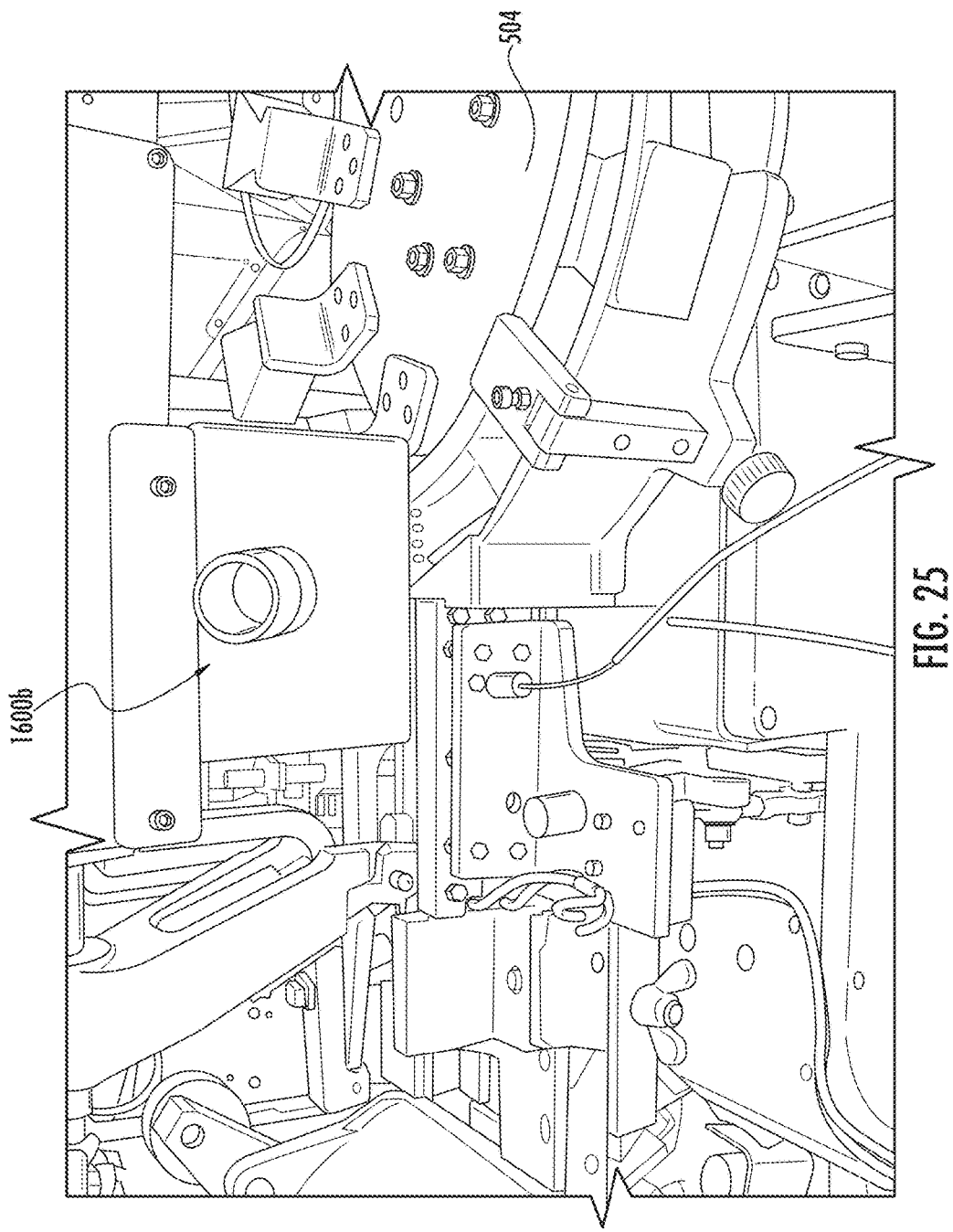
Figure 26:
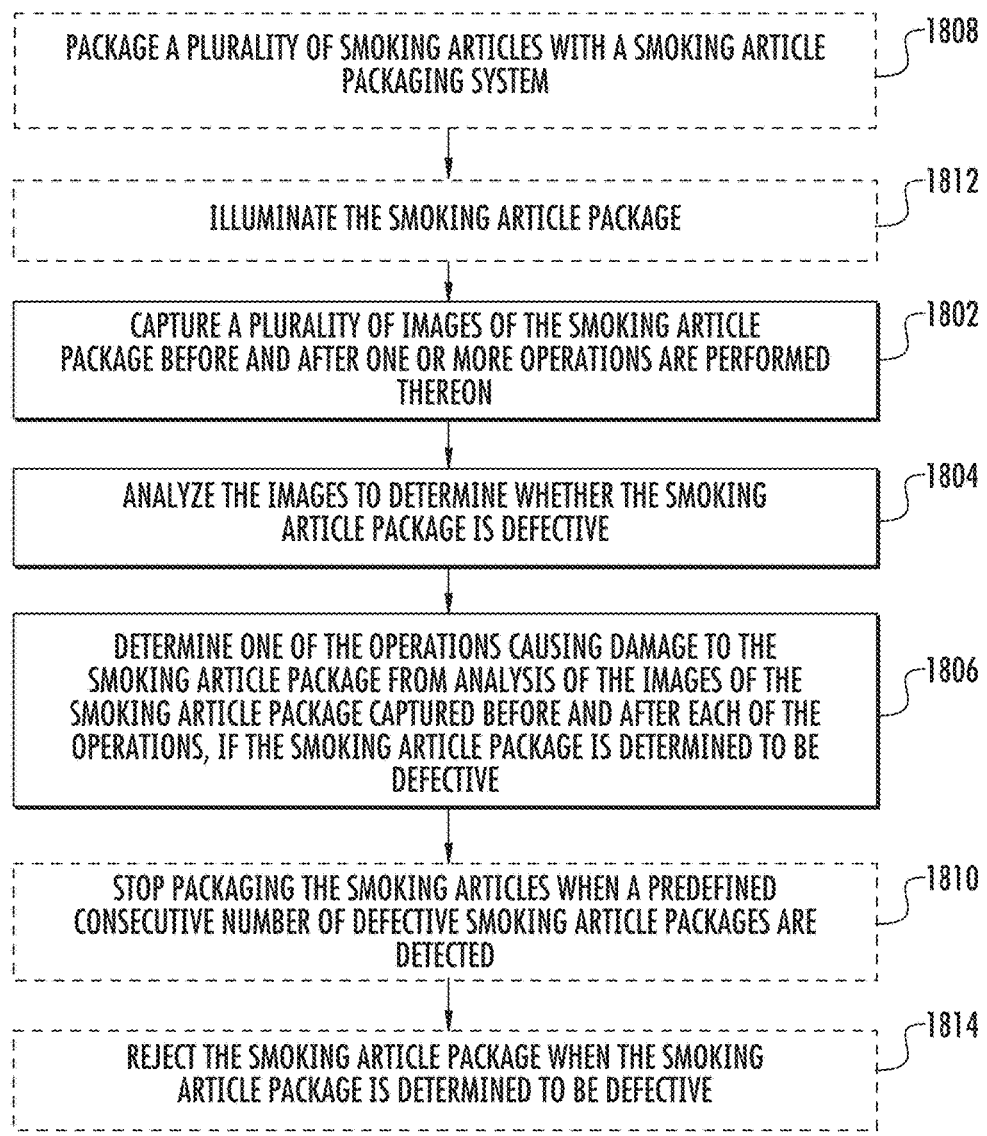

Having thus described the disclosure in the foregoing general terms, reference will now be made to the accompanying drawings, which are not necessarily drawn to scale, and wherein:

FIG. 1 schematically illustrates a system configured to produce packaged smoking articles according to an example embodiment of the present disclosure;

FIG. 2 illustrates an exploded view of a smoking article package according to an example embodiment of the present disclosure;

FIG. 3 illustrates a perspective view of the smoking article package of FIG. 2 in a closed configuration according to an example embodiment of the present disclosure;

FIG. 4 schematically illustrates a smoking article packaging system and a smoking article package inspection system of the system of FIG. 1 according to an example embodiment of the present disclosure;

FIG. 5 illustrates a side view of a first imaging device of the smoking article package inspection system of FIG. 4 according to an example embodiment of the present disclosure;

FIGS. 6A-D illustrate images captured by the first imaging device of FIG. 5 of smoking article packages including defects;

FIG. 7 illustrates a side view of a second imaging device of the smoking article package inspection system of FIG. 4 according to an example embodiment of the present disclosure;

FIG. 8 illustrates a front perspective view of the second imaging device of FIG. 7 according to an example embodiment of the present disclosure;

FIG. 9 illustrates a rear perspective view of the second imaging device of FIG. 7 according to an example embodiment of the present disclosure;

FIGS. 10A-H illustrate images captured by the second imaging device of FIG. 7 of smoking article packages including defects;

FIG. 11 illustrates a front perspective view of a third imaging device of the smoking article package inspection system of FIG. 4 according to an example embodiment of the present disclosure;

FIG. 12 illustrates a partial first side perspective view of the third imaging device of FIG. 11 according to an example embodiment of the present disclosure;

FIG. 13 illustrates a partial rear perspective view of the third imaging device of FIG. 11 according to an example embodiment of the present disclosure;

FIG. 14 illustrates a partial second side perspective view of the third imaging device of FIG. 11 according to an example embodiment of the present disclosure FIGS. 15A-D illustrate images captured by a first camera of the third imaging device of FIG. 11 of smoking article packages including defects;

FIGS. 16A-D illustrate images captured by a second camera of the third imaging device of FIG. 11 of smoking article packages including defects;

FIGS. 17A-D illustrate images captured by a third camera of the third imaging device of FIG. 11 of smoking article packages including defects;

FIGS. 18A-D illustrate images captured by a fourth camera of the third imaging device of FIG. 11 of smoking article packages including defects;

FIGS. 19A-D illustrate images captured by a fifth camera of the third imaging device of FIG. 11 of smoking article packages including defects;

FIG. 20 illustrates a side view of a first camera of a fourth imaging device of the smoking article package inspection system of FIG. 4 according to an example embodiment of the present disclosure;

FIGS. 21A-D illustrate images captured by the first camera of the fourth imaging device of FIG. 20 of smoking article packages including defects;

FIG. 22 illustrates a perspective view of a second camera of the fourth imaging device of the smoking article package inspection system of FIG. 4 according to an example embodiment of the present disclosure;

FIGS. 23A-D illustrate images captured by the second camera of the fourth imaging device of FIG. 22 of smoking article packages including defects;

FIG. 24 illustrates a perspective view of a heated air unit positioned after a wrapping wheel and prior to a double pack position according to an example embodiment of the present disclosure;

FIG. 25 illustrates a perspective view of a heated air unit located at a position at which two packaged smoking articles are stacked on top of one-another prior to placement in cartons by a cartoner according to an example embodiment of the present disclosure; and FIG. 26 schematically illustrates a method for inspecting a smoking article package according to an example embodiment of the present disclosure.

DETAILED DESCRIPTION OF THE ASPECTS OF THE DISCLOSURE

The present disclosure now will be described more fully hereinafter with reference to the accompanying drawing. The disclosure may be embodied in many different forms and should not be construed as limited to the aspects set forth herein; rather, these aspects are provided so that this disclosure will satisfy applicable legal requirements.

FIG. 1 illustrates a system 100 configured to produce packaged smoking articles 102. As illustrated, the system 100 may include a smoking article manufacturing system 104 configured to produce smoking articles 106, such as cigarettes. The smoking article manufacturing system 104 may comprise a conventional automated cigarette rod making machine. Exemplary cigarette rod making machines are of the type commercially available from Molins PLC or Hauni-Werke Korber & Co. KG. For example, cigarette rod making machines of the type known as MkX (commercially available from Molins PLC) or PROTOS (commercially available from Hauni-Werke Korber & Co. KG) can be employed. A description of a PROTOS cigarette making machine is provided in U.S. Pat. No. 4,474,190 to Brand, at col. 5, line 48 through col. 8, line 3, which is incorporated herein by reference. Types of equipment suitable for the manufacture of cigarettes also are set forth in U.S. Pat. No. 4,781,203 to La Hue; U.S. Pat. No. 4,844,100 to Holznagel; U.S. Pat. No. 5,156,169 to Holmes et al.; U.S. Pat. No. 5,191,906 to Myracle, Jr. et al.; U.S. Pat. No. 6,647,878 to Blau et al.; U.S. Pat. No. 6,848,449 to Kitao et al.; U.S. Pat. No. 6,904,917 to Kitao et al.; U.S. Pat. No. 7,210,486 to Hartman; U.S. Pat. No. 7,234,471 to Fitzgerald et al.; U.S. Pat. No. 7,275,548 to Hancock et al.; and U.S. Pat. No. 7,281,540 to Barnes et al., each of which is incorporated herein by reference.

The components and operation of conventional automated cigarette making machines will be readily apparent to those skilled in the art of cigarette making machinery design and operation. For example, descriptions of the components and operation of several types of chimneys, tobacco filler supply equipment, suction conveyor systems and garniture systems are set forth in U.S. Pat. No. 3,288,147 to Molins et al.; U.S. Pat. No. 3,915,176 to Heitmann et al; U.S. Pat. No. 4,291,713 to Frank; U.S. Pat. No. 4,574,816 to Rudszinat; U.S. Pat. No. 4,736,754 to Heitmann et al. U.S. Pat. No. 4,878,506 to Pinck et al.; U.S. Pat. No. 5,060,665 to Heitmann; U.S. Pat. No. 5,012,823 to Keritsis et al.; and U.S. Pat. No. 6,360,751 to Fagg et al.; and U.S. Patent Application Publication No. 2003/0136419 to Muller; each of which is incorporated herein by reference. The automated cigarette making machines of the type set forth herein provide a formed continuous cigarette rod or smokable rod that can be subdivided into formed smokable rods of desired lengths.

Various types of cigarette components, including tobacco types, tobacco blends, top dressing and casing materials, blend packing densities and types of paper wrapping materials for tobacco rods, can be employed. See, for example, the various representative types of cigarette components, as well as the various cigarette designs, formats, configurations and characteristics, that are set forth in Johnson, Development of Cigarette Components to Meet Industry Needs, 52nd T.S.R.C. (September, 1998); U.S. Pat. No. 5,101,839 to Jakob et al.; U.S. Pat. No. 5,159,944 to Arzonico et al.; U.S. Pat. No. 5,220,930 to Gentry; U.S. Pat. No. 6,779,530 to Kraker; U.S. Pat. No. 7,237,559 to Ashcraft et al.; and U.S. Pat. No. 7,565,818 to Thomas et al.; and U.S. Patent Application Publication Nos. 2005/0066986 to Nestor et al. and 2007/0246055 to Oglesby; each of which is incorporated herein by reference. Most preferably, the entire smokable rod is composed of smokable material (e.g., tobacco cut filler) and a layer of circumscribing outer wrapping material.

Components for filter elements for filtered cigarettes typically are provided from filter rods that are produced using traditional types of rod-forming units, such as those available as KDF-2 and KDF-3E from Hauni-Werke Korber & Co. KG. Typically, filter material, such as filter tow, is provided using a tow processing unit. An exemplary tow processing unit has been commercially available as E-60 supplied by Arjay Equipment Corp., Winston-Salem, N.C. Other exemplary tow processing units have been commercially available as AF-2, AF-3, and AF-4 from Hauni-Werke Korber & Co. KG. In addition, representative manners and methods for operating a filter material supply units and filter-making units are set forth in U.S. Pat. No. 4,281,671 to Byrne; U.S. Pat. No. 4,862,905 to Green, Jr. et al.; U.S. Pat. No. 5,060,664 to Siems et al.; U.S. Pat. No. 5,387,285 to Rivers; and U.S. Pat. No. 7,074,170 to Lanier, Jr. et al. Other types of technologies for supplying filter materials to a filter rod-forming unit are set forth in U.S. Pat. No. 4,807,809 to Pryor et al. and U.S. Pat. No. 5,025,814 to Raker; which are incorporated herein by reference.

The filter material can vary, and can be any material of the type that can be employed for providing a tobacco smoke filter for cigarettes. Preferably a traditional cigarette filter material is used, such as cellulose acetate tow, gathered cellulose acetate web, polypropylene tow, gathered cellulose acetate web, gathered paper, strands of reconstituted tobacco, or the like. Especially preferred is filamentary tow such as cellulose acetate, polyolefins such as polypropylene, or the like. One filter material that can provide a suitable filter rod is cellulose acetate tow having 3 denier per filament and 40,000 total denier. As another example, cellulose acetate tow having 3 denier per filament and 35,000 total denier can provide a suitable filter rod. As another example, cellulose acetate tow having 8 denier per filament and 40,000 total denier can provide a suitable filter rod. For further examples, see the types of filter materials set forth in U.S. Pat. No. 3,424,172 to Neurath; U.S. Pat. No. 4,811,745 to Cohen et al.; U.S. Pat. No. 4,925,602 to Hill et al.; U.S. Pat. No. 5,225,277 to Takegawa et al.; and U.S. Pat. No. 5,271,419 to Arzonico et al.; each of which is incorporated herein by reference.

Normally a plasticizer such as triacetin is applied to the filamentary tow in traditional amounts using known techniques. Other suitable materials or additives used in connection with the construction of the filter element will be readily apparent to those skilled in the art of cigarette filter design and manufacture. See, for example, U.S. Pat. No. 5,387,285 to Rivers; which is incorporated herein by reference in its entirety.

The plug wrap can vary. One example plug wrap is described in U.S. Pat. No. 4,174,719 to Martin, which is incorporated herein by reference. Typically, the plug wrap is a porous or non-porous paper material. Suitable plug wrap materials are commercially available. Exemplary plug wrap papers ranging in porosity from about 1,100 CORESTA units to about 26,000 CORESTA units are available from Schweitzer-Maudit International as Porowrap 17-M1, 33-M1, 45-M1, 70-M9, 95-M9, 150-M4, 150-M9, 240M9S, 260-M4 and 260-M4T; and from Miquel-y-Costas as 22HP90 and 22HP150. Non-porous plug wrap materials typically exhibit porosities of less than about 40 CORESTA units, and often less than about 20 CORESTA units. Exemplary non-porous plug wrap papers are available from Olsany Facility (OP Paprina) of the Czech Republic as PW646; Wattenspapier of Austria as FY/33060; Miquel-y-Costas of Spain as 646; and Schweitzer-Mauduit International as MR650 and 180. Plug wrap paper can be coated, particularly on the surface that faces the filter material, with a layer of a film-forming material. Such a coating can be provided using a suitable polymeric film-forming agent (e.g., ethylcellulose, ethylcellulose mixed with calcium carbonate, nitrocellulose, nitrocellulose mixed with calcium carbonate, or a so-called lip release coating composition of the type commonly employed for cigarette manufacture). Alternatively, a plastic film (e.g., a polypropylene film) can be used as a plug wrap material. For example, non-porous polypropylene materials that are available as ZNA-20 and ZNA-25 from Treofan Germany GmbH & Co. KG can be employed as plug wrap materials.

Manners and methods for applying adhesives to tipping materials during automated cigarette manufacture will be apparent to those skilled in the art of cigarette design and manufacture. For example, a filtered cigarette can be tipped with a first layer of tipping material in an essentially traditional manner using a Lab MAX tipping device that is available from Hauni-Werke Korber & Co. KG, and that tipped cigarette can be collected and tipped again using that device (e.g., using the device in an essentially traditional manner, or in a suitably modified manner to provide a desired pattern of adhesive application) in order to provide a filtered cigarette possessing two layers of tipping material.

The tipping material that is used for any of the tipping material layers can vary. In certain preferred aspects, the material used to construct both tipping material layers has the characteristics and qualities commonly associated with cigarette tipping materials known in the art. As such, both layers can be constructed of the types of material conventionally used as tipping material in the manufacture of cigarettes. Typical tipping materials are papers exhibiting relatively high opacities. Representative tipping materials have TAPPI opacities of greater than about 81 percent, often in the range of about 84 percent to about 90 percent, and sometimes greater than about 90 percent. Typical tipping materials are printed with inks, typically nitrocellulose based, which can provide for a wide variety of appearances and "lip release" properties. Representative tipping papers materials have basis weights ranging from about 25 $g/m^2$ to about 60 $g/m^2$, often about 30 $g/m^2$ to about 40 $g/m^2$. Representative tipping papers are available as Tervakoski Reference Nos. 3121, 3124, TK 652, TK674, TK675, A360 and A362; and Schweitzer-Mauduit International Reference Nos. GSR270 and GSR265M2. See also, for example, the types of tipping materials, the methods for combining cigarette components using tipping materials, and techniques for wrapping various portions of cigarettes using tipping materials, that are set forth in U.S. Patent Application Publication No. 2007/0215167 to Crooks et al., which is incorporated herein by reference in its entirety.

Adhesives used to secure tipping materials to each other or to other filtered cigarette components can vary. Typical exemplary adhesive formulations that are used for application of tipping material to other cigarette components in commercial filtered cigarette manufacturing operations are water-based emulsions incorporating mixtures of ethylene vinyl acetate copolymers and polyvinylacetate. Representative adhesives that are useful for applying tipping materials to cigarette components are available as Reference Nos. 32-2049 and 32-2124 from National Starch & Adhesives Corp. See also, for example, Skeist, Handbook of Adhesives, 2nd Edition (1977); Schneberger, Adhesive in Manufacturing (1983); Gutcho, Adhesives Technology Developments Since 1979 (1983); Landrock, Adhesives Technology Handbook (1985); and Flick, Handbook of Adhesives Raw Materials, 2nd Edition (1989).

Thus, the smoking articles 104 may be produced using, for example, an embodiment of a smoking article manufacturing system 104 as described above. Thereafter, the smoking articles 106 may be packaged to form the packaged smoking articles 102. In this regard, as illustrated in FIG. 1, the system 100 may further comprise a smoking article packaging system 108. Example embodiments of smoking article packaging systems are described in U.S. Pat. No. 7,325,382 to Nelson et al. and U.S. Pat. No. 7,866,122 to Pipes et al., which are incorporated herein by reference in their entireties.

Accordingly, the as-formed smoking articles 106 may be loaded into an appropriately-sized package. In this regard, FIG. 2 illustrates an example embodiment of a smoking article package 200. The smoking article package 200 may include an outer body 202 and an inner frame 204. In some embodiments the outer body 202 and the inner frame 204 may be formed from paperboard. The outer body 202 includes a front wall 206, a back wall 208, a right sidewall 210 connecting the front wall to the back wall, a left sidewall 212 connecting the front wall to the back wall, and a bottom wall 214 that closes the opening formed by the front wall, back wall, right sidewall and left sidewall. For purposes of illustration, a portion of the front wall 206 is shown cut away, as is a portion of the inner frame 204. The front wall 206, back wall 208, right sidewall 210, left sidewall 212, and bottom wall 214 together form a volume closed at one end and having a rectangular cross-section. The outer body 202 forms a top opening 216 opposite the bottom wall 214.

The outer body 202 further comprises a lid 218. The lid 218 is formed having a front wall 220, a back wall 222, a right sidewall 224 that connects the front wall and back wall, and a left sidewall 226 that also connects the front wall and the back wall. The lid 218 defines a rectangular cross-section of similar size and shape to the cross-section of the body 202. The lid 218 includes a top wall 228 closing off the rectangular cross section. Preferably, the lid 218 is hingedly attached to the outer body 202 by a hinge 230 that is integral with the back wall 208 of the outer body 202 and the back wall 222 of the lid 218. The hinge 230 is preferably formed by a crease or scoring or perforation in the material of the back wall 208 of the outer body 202 and the back wall 222 of the lid 218. The hinge 230 delimits each back wall 208, 222.

Preferably, the lid 218 is integrally connected with the outer body 202 as shown in FIG. 2, so that it may be movable between an open position and a closed position without being physically separated from the outer body. However, those skilled in the art understand that the lid 218 may be composed of a separate portion that is hingedly connected to the outer body 202 by extra tab portions. These tab portions may be adhesively or otherwise connected to the inner surfaces of the outer body 202 and lid 218. The lid 218 preferably is movable relative to the outer body 202, in order to manipulate the smoking article package 200 between open and closed configurations. The lid 218 most preferably is adapted to cooperate with the outer body 202, and hence, act to cover the top region of the outer body (e.g., the lid 218 can fit over the top region of the outer body, and can be maintained in place, such as by friction fit between the outer surface of the inner frame 204 and the inner surface of the sidewalls 224, 226 of the lid 218, such as in the manner described above), and hence, retain the smoking article package 200 in the closed configuration.

A plurality of smoking articles 106 may thus be loaded into the smoking article package 200. However, as illustrated, the smoking articles 106 may be wrapped with an inner wrapper 232 prior to insertion into the smoking article package 200 in some embodiments. In one embodiment the inner wrapper 232 may comprise a foil-type material (e.g., a laminated metal foil/paper liner material). See, for example, U.S. Pat. No. 7,325,368 to Miyaoka et al., which is incorporated herein by reference in its entirety. An insert 234 (e.g., an insert including warnings or information regarding the smoking articles 106) may also be provided within the smoking article package. If desired, the completed smoking article package can be wrapped in an outer wrapper (e.g., a clear polypropylene film). If desired, the smoking article package can be or imprinted with an indicia before and/or after being wrapped with the outer wrapper.

FIG. 3 illustrates the smoking article package 200 in a closed configuration. As illustrated, in some embodiments the smoking article package 200 may define a generally rectilinear configuration defining six sides. More particularly, the smoking article package may include a bottom wall 242, a top wall 244, a left wall 246, a right wall 248, a front wall 250, and a back wall 252.

However, various other embodiments of smoking articles packages may be employed to package smoking articles. In this regard, other representative types of smoking packages suitable for use with the present disclosure include, for example, those of the types set forth in U.S. Pat. No. 4,294,353 to Focke et al.; U.S. Pat. No. 4,534,463 to Bouchard; U.S. Pat. No. 4,715,497 to Focke et al.; U.S. Pat. No. 4,852,734 to Allen et al.; U.S. Pat. No. 5,139,140 to Burrows et al.; U.S. Pat. No. 5,333,729 to Wolfe; U.S. Pat. No. 5,938,018 to Keaveney et al.; U.S. Pat. No. 6,726,006 to Funderburk et al.; U.S. Pat. No. 6,736,261 to Thomas et al.; U.S. Pat. No. 7,014,039 to Henson et al.; U.S. Pat. No. 7,325,382 to Nelson et al.; U.S. Pat. No. 7,617,930 to Jones et al.; and U.S. Pat. No. 7,823,731 to Wu; PCT WO 2005/113386 to Buse; UK Patent Spec. 1,042,000; German Patent Application DE 10238906 to Marx; and US Patent Application Publication Nos. 2004/0217023 to Fagg et al.; 2005/0150786 to Mitten et al.; 2008/0099353 to Parsons et al.; and 2008/0230410 to Jones et al., which are incorporated herein by reference in their entireties. In some instances, the smoking article package may be of the type that has been referred to as a "shoulder box," of which many types have been commercially available.

As illustrated in FIG. 1, in some embodiments the system 100 configured to produce packaged smoking articles 102 may further comprise a smoking article package inspection system 110. In this regard, certain defects may occur during packaging of the smoking articles 106, which may provide the packaged smoking articles 102 with an undesirable appearance. Accordingly, the smoking article package inspection system 110 may inspect the packaged smoking articles 102 before and/or after completion thereof.

In this regard, FIG. 4 illustrates a more detailed view of the smoking article packaging system 108 and the smoking article package inspection system 110. As illustrated, the smoking article packaging system 108 may include a packing unit 300, a printing unit 400, and a wrapping unit 500. The packing unit 300 may be configured to pack (e.g., enclose) a plurality of smoking articles 106 in the smoking article package 200 to form a packed smoking article package 236. Example embodiments of methods and apparatuses for packing smoking articles in a smoking article package are disclosed in U.S. Pat. No. 7,325,382 to Nelson et al., which is incorporated herein by reference.

The printing unit 400 may be configured to print an identifier 238 on a smoking article package (e.g. on the packed smoking article package 236). In some instances, the printing unit may comprise a laser or inkjet printer capable of being controlled by a computer device to print the identifier 238 on the smoking article package. The identifier 238 may comprise a unique identifier including information such as a time and location of manufacture, in any form (e.g., a universal product code, a bar code, an alphanumeric a character string, and/or a symbol), identifying the smoking article package on which the identifier is printed. In other embodiments the identifier 238 may include more generic information such as the manufacturer, brand, flavor etc. of the smoking articles in the smoking article package. Example embodiments of methods and apparatuses for printing on smoking article packages are disclosed in U.S. Patent Application Publication Nos. 2010/0186351 to Carter et al. and 2013/0096711 to Gates et al., each of which is incorporated herein by reference in its entirety.

The wrapping unit 500 may be configured to wrap a smoking article package (e.g., the packed smoking article package 236) with an outer wrapper 240 to complete the packaged smoking article 102. Example embodiments of methods and apparatuses for wrapping smoking article packages are disclosed in U.S. Pat. Nos. 7,762,046 and 7,866,122 to Pipes et al., each of which is incorporated herein by reference in its entirety. Note that although the printing unit 400 is illustrated as being positioned downstream of the packing unit 300 and upstream of the wrapping unit 500, in other embodiments the printing unit may alternatively or additionally be configured to print on wrapper 240 after the smoking article package is wrapped by the wrapping unit.

As further illustrated in FIG. 4, the smoking article package inspection system 110 may comprise a plurality of imaging devices 600a-d and an analysis unit 602. The imaging devices 600a-d may be configured to capture a plurality of images of a smoking article package during and after completion of the packaged smoking article 102, including packaging of smoking articles. The analysis unit 602 may be configured to analyze the images captured by the imaging devices and determine whether the smoking article package is defective. In some embodiments the smoking article package inspection system 110 may further comprise one or more illumination devices such as one or more light bulbs or strobe lights 604a-d. The strobe lights 604a-d may be configured to illuminate the smoking article package at the imaging devices 600a-d. In this regard, the strobe lights 604a-d may be timed to flash when the smoking article packages pass in front of the imaging devices 600a-d. However, in other embodiments ambient light may be sufficient, or illumination devices may provide substantially constant illumination of the smoking article packages.

The imaging devices may comprise cameras configured to capture images of smoking article packages in the visible spectrum. Thus, for example, the imaging devices may capture images of the exposed outer portion of the smoking article packages. Examples of imaging devices configured to capture images in the visible spectrum are commercially available from Cognex Corporation of Natick, Mass. However, in other embodiments the imaging devices may be configured to capture images outside of the visible spectrum. For example, the imaging devices may capture infrared or ultraviolet images. In some embodiments the imaging devices may be configured to capture images of internal portions of smoking article packages using, for example, x-rays or magnetic resonance imaging.

The imaging devices 600a-d may be positioned and configured, by way of example, to capture images of a smoking article package before and after enclosing a plurality of smoking articles in the smoking article package, before and after printing an identifier on the smoking article package, and/or before and after wrapping the smoking article package with an outer wrapper. Note that although the images are described herein as being captured before and after certain referenced events, it should be understood that such language includes embodiments and situations in which a smoking article package is removed from production prior to the referenced event occurring. In this regard, as described below, in some instances defective smoking article packages may be removed by a rejecting unit. For example, after a first image is captured of a smoking article package, it may be apparent that the smoking article package is defective. Accordingly, the defective smoking article package may be removed prior to any further processing thereon and/or capturing of a second image thereof. In this regard, the above-referenced language reciting capturing images before and after a referenced event refers to events occurring on packages that are not determined to be defective in regard to the original/first image, whereas events occurring in relation to defective smoking article packages may or may not differ from the above-referenced language reciting capturing images before and after a referenced event.

In the illustrated embodiment the smoking article package inspection system 110 comprises four imaging devices 600a-d. However, it should be understood that a greater or lesser number of imaging devices may be employed. More particularly, the illustrated embodiment of the smoking article package inspection system 110 includes a first imaging device 600a positioned at the packing unit 300. Thus, in some embodiments the imaging device 600a may be positioned and configured to capture images of the smoking article package before or during enclosing a plurality of smoking articles in the smoking article package, before printing an identifier on the smoking article package, and before wrapping the smoking article package with an outer wrapper. However, it should be understood that the relative placement of the packing unit 300, the printing unit 400 and the wrapping unit 500 may vary from the illustrated configuration.

The analysis unit 602 may be configured to analyze the images captured at the packing unit 300 to determine whether the smoking article package is defective. Analyzing the images of the smoking article package may include analyzing one or more of the inner frame 204, the inner wrapper 232, the smoking articles 106, the insert 234, and the outer body 202. In this regard, in one embodiment the analysis unit 602 may be configured to determine whether the smoking article package is missing the inner frame 204, whether the inner frame is misaligned, whether the smoking article package is missing the insert 234, whether the insert is misaligned, and/or whether the inner wrapper 232 surrounding the smoking articles 106 is damaged. However, various alternate or additional defects may be detected in other embodiments.

An example configuration of the first imaging device 600a at the packing unit 300 is illustrated in FIG. 5. As illustrated, the first imaging device 600a may be positioned above a folding wheel 302 of the packing unit 300 at which the outer body 202 is folded to form the smoking article package (see, e.g., FIG. 4). More particularly, the folding wheel 302 illustrated in FIG. 5 is the last wheel of the packing unit 300. In this regard, the folding wheel 302 folds the outer body 202 around the smoking articles 106 to form the front and back of the packed smoking article package 236. The one or more strobe lights 604a may illuminate the smoking article packages as they pass the first imaging device 600a at the folding wheel 302 such that the imaging device may capture one or more images of each smoking article package passing thereby. Thus, the first imaging device 600a may capture images at substantially the last possible time and location prior to completely wrapping the outer body 202 around the periphery of the smoking articles 106. Thus, the first imaging device 600a may be positioned at the last location at which images may be captured of the longitudinal length of the smoking articles 106 within the outer body 202, which may be useful to ensure proper placement of the smoking articles within the outer body 202.

FIGS. 6A-D are images 700a-d captured by the first imaging device 600a positioned at the packing unit 300. As shown, the first imaging device 600a may capture images of the inner frame 204, the inner wrapper 232, the insert 234, and the outer body 202. In the illustrated embodiment, the images 700a-d are captured prior to enclosing the smoking articles. In this regard, the outer body 202 of the smoking article package does not yet fully enclose the smoking articles 106. However, the smoking articles 106 may be wrapped by an inner wrapper 232 prior to being fully enclosed by the outer body 202, as illustrated.

Figure 6A:
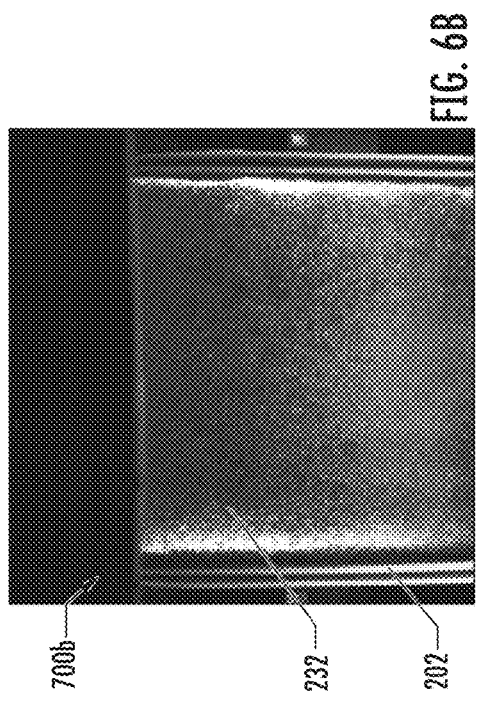
Figure 6C:
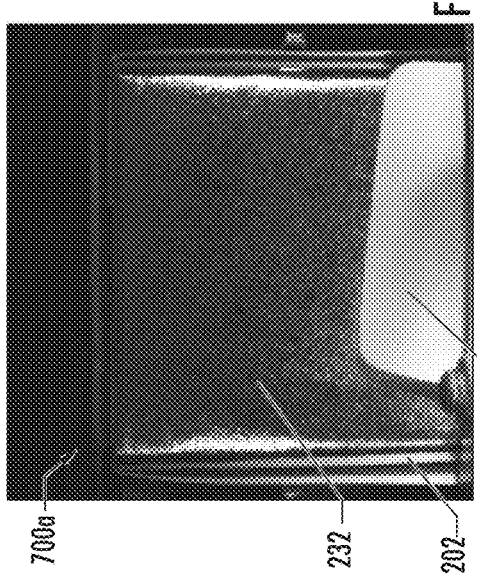
Figure 6B:
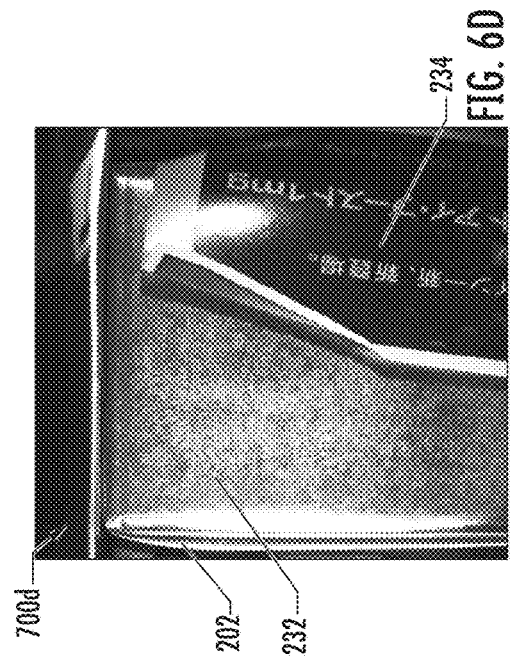
Figure 6D:
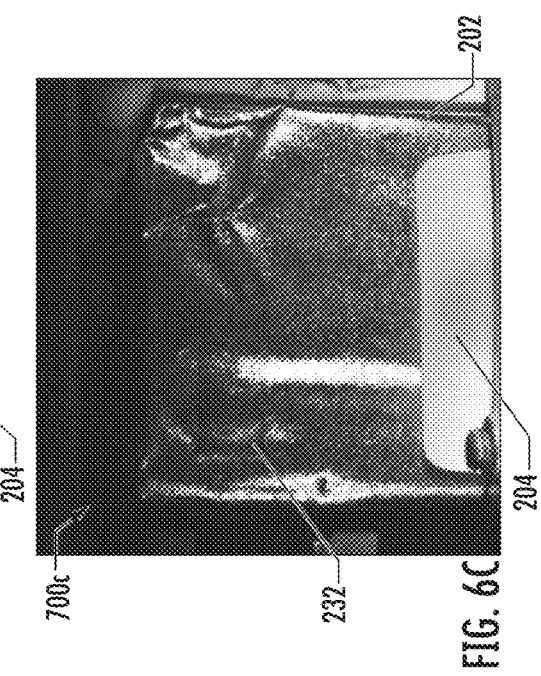

The images 700a-d of smoking article packages include defects which the analysis unit 602 may detect. In this regard, FIG. 6A illustrates an image 700a in which the inner frame 204 is misaligned. FIG. 6B illustrates an image 700b in which the inner frame 204 is missing. FIG. 6C illustrates an image 700c in which the inner wrapper 232 is damaged (e.g., wrinkled/crushed). FIG. 6D illustrates an image 700d in which the insert 234 is misaligned. Accordingly, images may be captured by the first imaging device 600a positioned at the packing unit 300 and the images may be analyzed by the analysis unit 602 to detect defects such as those shown in FIGS. 6A-D.

As illustrated in FIG. 4, the smoking article package inspection system 110 may further comprise imaging devices 600b-d positioned downstream of the packing unit 300. For example, in the illustrated embodiment, a second imaging device 600b may be positioned at or downstream of the printing unit 400. In the illustrated embodiment, the second imaging device 600b is positioned to capture images after enclosing a plurality of smoking articles in the smoking article package, after printing an identifier on the smoking article package, and before wrapping the smoking article package with an outer wrapper, although the images captured may depend on the particular arrangement of the components of the smoking article packaging system 108. The analysis unit 602 may be configured to analyze the images captured by the second imaging device 600b to determine whether the smoking article package is defective.

As illustrated in FIG. 4, analyzing the images of the smoking article package may include analyzing the packed smoking article package 236 during or after printing the identifier 238 thereon. In this regard, in one embodiment the analysis unit 602 may be configured to determine whether the identifier 238 is illegible, whether the identifier is missing print, whether the identifier is misaligned, whether the identifier is of poor quality, and/or whether the identifier includes incorrect information. Such defects may include an identifier entirely missing from the smoking article package, an identifier that is compressed, distorted, or otherwise smudged such that the identifier is rendered illegible, or an identifier having any other characteristic affecting the readability thereof. However, the analysis unit 602 may be configured to detect various other defects that may be associated with printing the identifier.

An example configuration of the second imaging device 600b is illustrated in FIGS. 7 and 8. As illustrated, the second imaging device 600b may be positioned downstream of the printing unit 400. In one embodiment, as illustrated, both the second imaging device 600b and the printing unit 400 may be positioned within a casing 606. The casing 606 may include a lid 608 which, when closed, may substantially seal the casing shut. Thereby, user contact with moving parts in the casing 606 may be avoided. Further, lighting conditions within the casing 606 may be standardized by substantially sealing out external light. In this regard, light within the closed casing 606 may be provided by one or more strobe lights 604b (see, FIG. 4) or other illumination sources.

As illustrated, the second imaging device 600b may be positioned proximate the packed smoking article packages 236 such that the identifier 238 is visible. More particularly, the packed smoking article packages 236 may be received in a delivery conduit 610, as illustrated in FIGS. 7-9. The packed smoking article packages 236 may be transported therethrough using, for example, one or more conveyor belts. In the illustrated embodiment, opposing conveyor belts 612 configured to move in the same direction transport the packed smoking article packages 236 through the delivery conduit 610. The packed smoking article packages 236 may be oriented in the delivery conduit 610 between the conveyor belts 612 such that the bottom 242 thereof faces an opening 614 in the casing 606. Thereby, the printing unit 400, which may comprise a printing head (e.g., a laser or inkjet head), may print the identifier 238 on the bottom 242 of the packed smoking article packages 236 through the opening 614 in the casing 606.

The second imaging device 600b may be positioned downstream of the printing unit 400 and oriented toward the opening 614 in the casing 610. Additionally, one or more sensors 616 (e.g., light or laser optical sensors) may be configured to detect the packed smoking article packages 236 in the delivery conduit 610. More particularly, the sensors 616 may detect each of the packed smoking article packages 236 (e.g., by detecting gaps between the smoking article packages, the external boundaries of the smoking article packages, or other features thereof). Accordingly, the one or more strobe lights 604b (see, e.g., FIG. 4) may illuminate the smoking article packages as they pass the second imaging device 600b such that the second imaging device may capture one or more images of each packed smoking article package passing thereby. In this regard, the strobe lights 604b (see, FIG. 4) and the second imaging device 600b may be triggered by the sensors 616 to illuminate the packed smoking article packages and capture images thereof.

Note that the packed smoking article packages 236 may be transported past the printing unit 400 and the second imaging device 600b in other manners. For example, the packed smoking article packages 236 may be transported by a single conveyor belt. However, use of the opposing conveyor belts 612, each moving in the same direction at the same speed, may grasp the packed smoking articles 236 therebetween and provide the packed smoking articles with stability that may improve printing thereon by the printing unit 400 and improve the images of the packed smoking article packages by reducing movement thereof in undesirable directions.

FIGS. 10A-H are images 800a-h captured by the second imaging device 600b positioned at or downstream of the printing unit 400. As shown, the second imaging device 600b may capture images of the identifier 238. In the illustrated embodiment the identifier 238 is printed on the bottom 242 of the smoking article package. However, the second imaging device 600b may capture images of identifiers on various other portions of the smoking article package.

Figure 10:
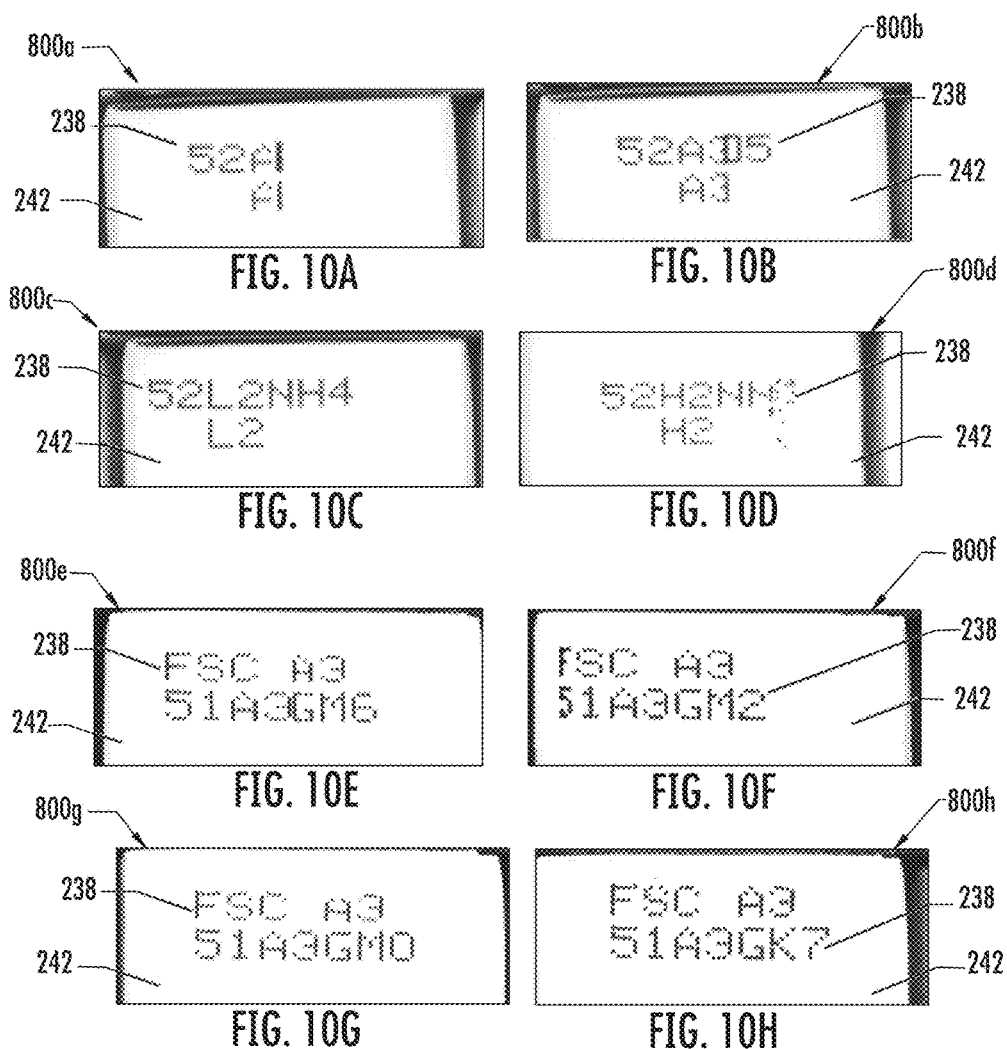

The images 800a-h of smoking article packages in FIGS. 10A-H include defects which the analysis unit 602 may detect. In this regard, FIG. 10A illustrates an image 800a in which the identifier 238 is missing print. FIG. 10B illustrates an image 800b in which the identifier 238 includes illegible print. FIG. 108C illustrates an image 800c in which the identifier 238 is misaligned (e.g., not properly centered). FIG. 10D-F illustrate images 800d-f in which the identifier 238 includes illegible print. FIG. 10G illustrates an image 800g in which the identifier 238 is poorly printed (e.g., the identifier may be printed with insufficient contrast). FIG. 10H illustrates an image 800h in which the identifier 238 includes an illegible character. Accordingly, images may be captured by the second imaging device 600b positioned at or downstream of the printing unit 400 and the images may be analyzed by the analysis unit 602 to detect defects such as those shown in FIGS. 10A-H.

As illustrated in FIG. 4, a third imaging device 600c may be positioned downstream of the packing unit 300. In the illustrated embodiment, the third imaging device 600c is positioned to capture images after enclosing a plurality of smoking articles in the smoking article package, after printing an identifier on the smoking article package, and before wrapping the smoking article package with an outer wrapper, although the images captured may depend on the particular arrangement of the components of the smoking article packaging system 108. The analysis unit 602 may be configured to analyze the images captured by the third imaging device 600c to determine whether the smoking article package is defective.

Analyzing the images of the smoking article package with the third imaging device 600c may include analyzing the packed smoking article package 236 during or after printing the identifier 238 thereon. Thus, in some embodiments the third imaging device 600c may be configured to capture images of the smoking article packages at substantially the same stage in the production thereof as the second imaging device 600b and hence the analysis unit 602 may determine defects associated with printing an identifier as discussed above. However, the third imaging device may be configured to capture images of various other portions of the smoking article packages such that the analysis unit 602 may detect various other defects. In this regard, in one embodiment the analysis unit 602 may employ images captured by the third imaging device 600c to determine whether a flap of the smoking article package is open, whether a lid of the smoking article package is open, whether an ear of the smoking article package is open, whether the identifier is illegible, whether the identifier is missing print, whether the identifier is misaligned, whether the identifier is of poor quality, whether the identifier includes incorrect information, whether the smoking article package is damaged, whether the smoking article package is contaminated, and/or whether the smoking article package is improperly positioned. However, the analysis unit 602 may be configured to detect various other defects that may be associated with printing the identifier and/or enclosing the smoking articles.

An example configuration of the third imaging device 600c positioned downstream of the packing unit 300 is illustrated in FIGS. 11-14. As illustrated, in one embodiment the third imaging device 600c may include multiple cameras 600c1-5 or other imaging devices configured to capture images of multiple sides of the smoking article package. As illustrated, the cameras 600c1-5 may be positioned within a casing 624. The casing 624 may include one or more see-through panels 626 (e.g., translucent or transparent panels) which, when closed, may substantially seal the casing 624 shut. Thereby, user contact with moving parts in the casing 624 may be avoided.

The packed and printed smoking article packages 236 may be directed through the casing 624 to a position at which images thereof may be captured. For example, the packed and printed smoking article packages 236 may be transported therethrough using a conveyor belt 628, on which the smoking article packages may rest. Additionally, one or more sensors 630 (e.g., laser or light optical sensors) may be configured to 630 may detect each of the packed and printed smoking article packages 236 (e.g., by detecting a smoking article package breaking a light beam extending across a path of the conveyor belt 628). Accordingly, the cameras 600c1-5 may capture images of the smoking article packages 236.

More particularly, a first camera 600c1 may capture an image of the top 244 of the smoking article package, a second camera 600c2 may capture an image of the back 252 of the smoking article package, a third camera 600c3 may capture an image of the bottom 242 of the smoking article package, a fourth camera 600c4 may capture an image of the front 250 of the smoking article package, and a fifth camera 600c5 may capture an image of a side (e.g., right side 248) of the smoking article package. An additional camera may also capture an image of an opposing side (e.g., left side 246) of the smoking article package such that the third imaging device 600c may capture images of each of the six sides of the smoking article package. Accordingly, the one or more strobe lights 604c (see, e.g., FIG. 4) may illuminate the smoking article packages as they pass the cameras 600c1-5 of the third imaging device 600c such that the imaging device may capture one or more images of each smoking article package passing thereby.

Figure 15D:
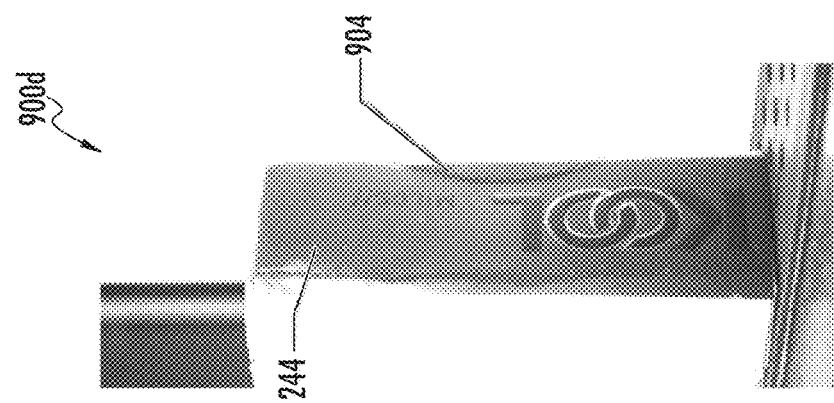
Figure 15C:
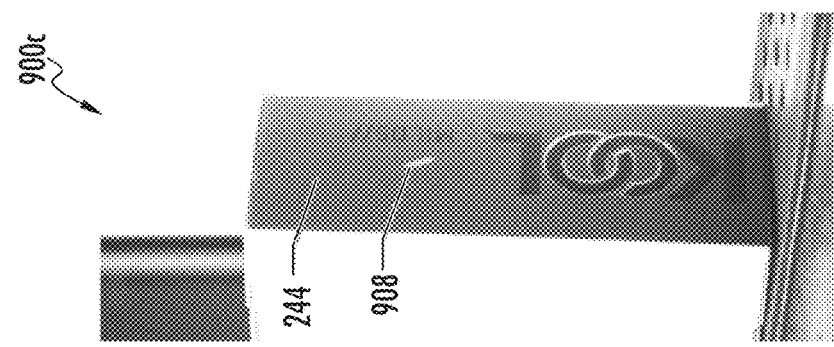
Figure 15B:
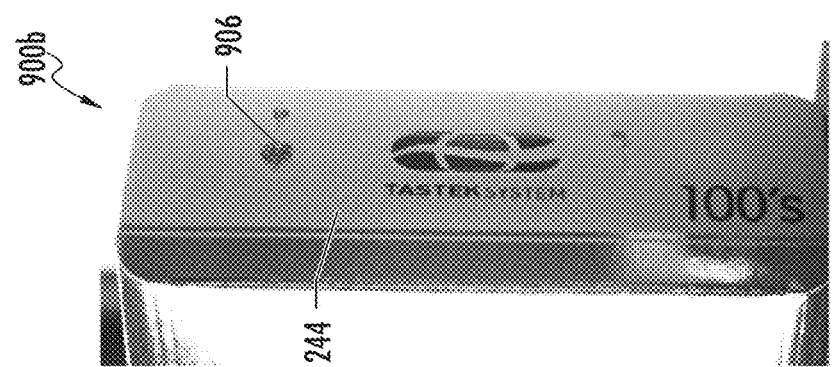
Figure 15A:
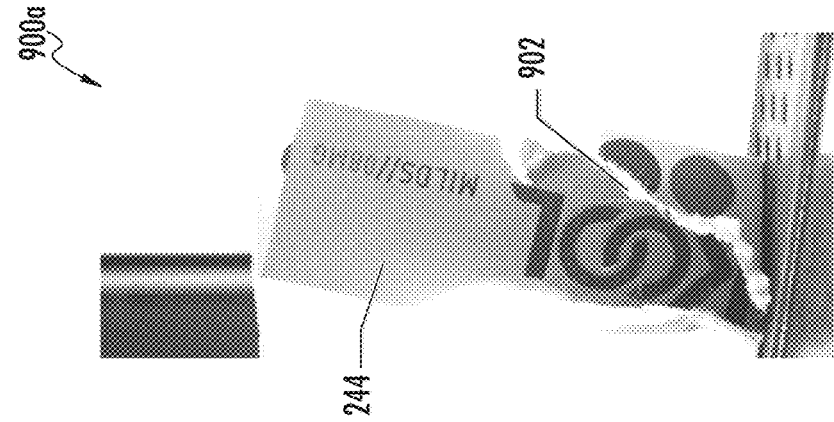

FIGS. 15A-D show images 900a-d captured by the first camera 600c1 of the third imaging device 600c. As shown, the first camera 600c1 of the third imaging device 600c may capture images of the top 244 of the smoking article package. The images 900a-d of the top 244 of the smoking article packages include defects which the analysis unit 602 may detect. In this regard, FIGS. 15A and 15D illustrate images 900a, 900d in which the top 244 of the smoking article package includes damage 902, 904 (e.g., torn or crushed material). Further, FIGS. 15B and 15C illustrate images 900b, 900c in which there are contaminants 906, 908 (e.g., smeared ink or trash) on the top 244 of the smoking article package.

Figure 16A:
Figure 16B:
Figure 16C:
Figure 16D:

FIGS. 16A-D show images 1000a-d captured by the second camera 600c2 of the third imaging device 600c. As shown, the second camera 600c2 of the third imaging device 600c may capture images of the back 252 of the smoking article package. The images 1000a-d of the back 252 of the smoking article packages include defects which the analysis unit 602 may detect. In this regard, FIGS. 16A-C illustrate images 1000a-c in which the back 252 of the smoking article package includes damage 1002, 1004, 1006 (e.g., missing, torn, or dislodged material). Further, FIG. 16D illustrates an image 1000d in which the smoking article package includes an open side flap 1008.

FIGS. 17A-D show images 1100a-d captured by the third camera 600c3 of the third imaging device 600c. As shown, the third camera 600c3 of the third imaging device 600c may capture images of the bottom 242 of the smoking article package. The images 1100a-d of the bottom 242 of the smoking article packages include defects which the analysis unit 602 may detect. In this regard, FIGS. 17A and 17D illustrate images 1100a, 1100d in which the bottom 242 of the smoking article package includes damage 1102, 1104 in the form of scratches. Further, FIG. 17B illustrates an image 1100c in which the bottom 242 of the smoking article package includes damage 1106 in the form of a crushed region. FIG. 17C illustrates an image 1100d in which the bottom 242 of the smoking article package includes print 1108 of poor quality (e.g., misaligned/shifted print).

Figure 18B:
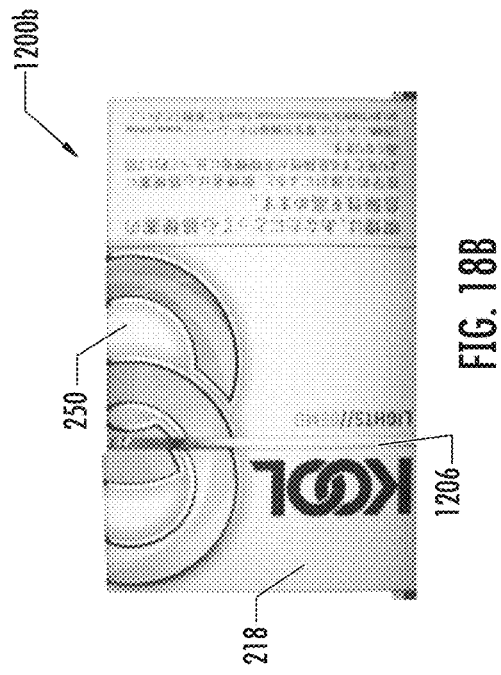
Figure 18D:
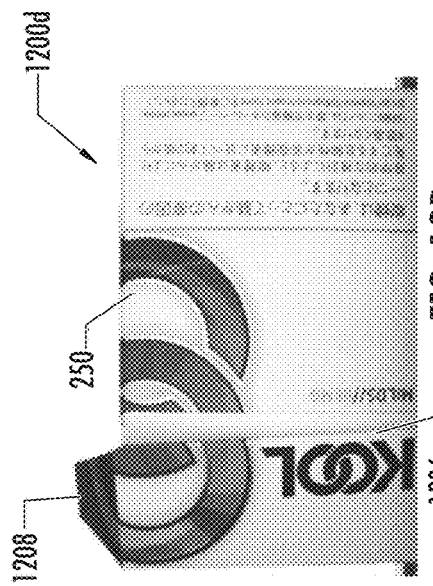
Figure 18A:
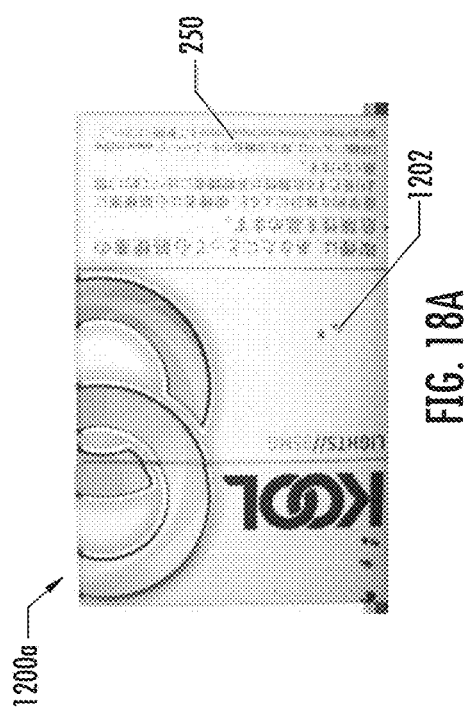
Figure 18C:

FIGS. 18A-D show images 1200a-d captured by the fourth camera 600c4 of the third imaging device 600c. As shown, the fourth camera 600c4 of the third imaging device 600c may capture images of the front 250 of the smoking article package. The images 1200a-d of the front 250 of the smoking article packages include defects which the analysis unit 602 may detect. In this regard, FIGS. 18A and 18C illustrate images 1200a, 1200c in which there are contaminants 1202, 1204 (e.g., dirt and discoloration) on the front 250 of the smoking article package. Further, FIGS. 18B and 18D illustrate images 1200b, 1200d showing defects in the form of an open lid 1206. The image 1200d illustrated in FIG. 18D also shows a defect in the form of an open ear 1208 of the lid.

FIGS. 19A-D show images 1300a-d captured by the fifth camera 600c5 of the third imaging device 600c. The fifth camera 600c5 of the third imaging device 600c may capture images of one the sides 246, 248 of the smoking article package. Optionally a sixth camera of the third imaging device 600c may capture images of the other side of the smoking article package. For example, in the illustrated embodiment the fifth camera 600c5 has captured images 1300a-d of the right side 248 of the smoking article package, whereas a sixth camera may optionally capture images of the opposing left side 246.

Figure 19A:
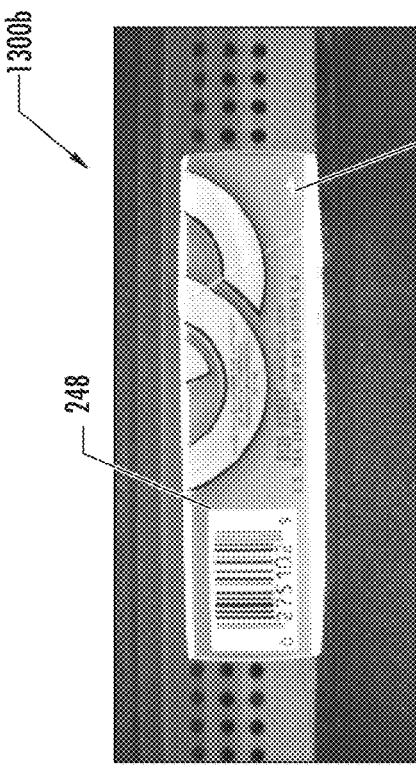
Figure 19B:
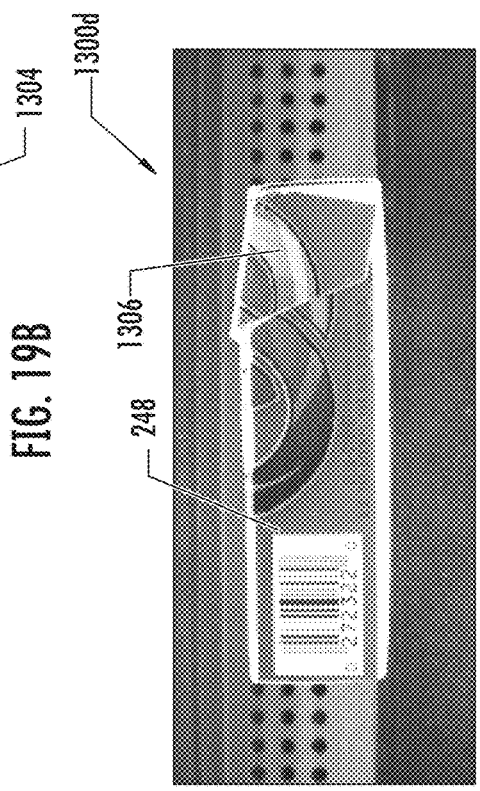
Figure 19C:
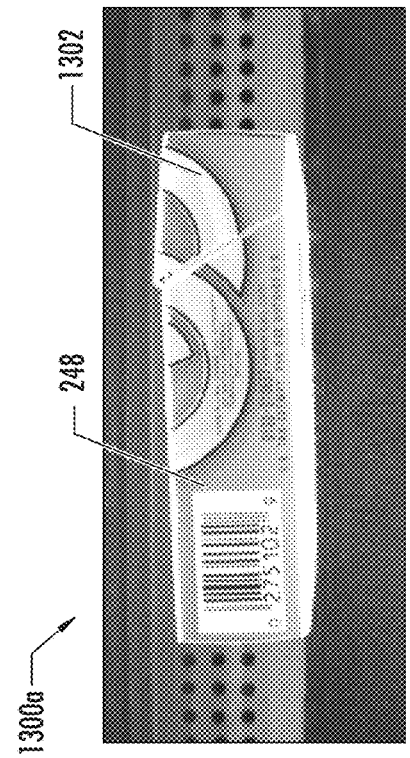
Figure 19D:
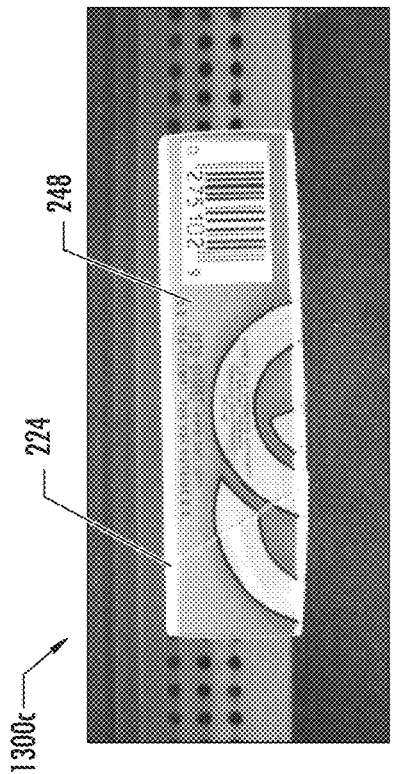

The images 1300a-d of the side 248 of the smoking article packages include defects which the analysis unit 602 may detect. In this regard, FIG. 19A illustrates an image 1300a showing a defect in the form of an open lid 1302. FIG. 19B illustrates an image 1300b showing a defect in the form of damage 1304 (e.g., a scuff or scratch) on the smoking article package. FIG. 19C illustrates an image 1300c showing a defect in the form of a smoking article package that is improperly positioned (e.g., hinge 230 is positioned at the top of the image, whereas it should be positioned at the bottom). FIG. 19D illustrates an image 1300d showing a defect in the form of an open ear 1306 of the lid. Accordingly, images may be captured by cameras 600c1-600c5 of the third imaging device 600c positioned downstream of the packing unit 300 and the images may be analyzed by the analysis unit 602 to detect defects such as those shown in FIGS. 19A-D.

As illustrated in FIG. 4, a fourth imaging device 600d may be positioned at or downstream of the wrapping unit 500 configured to wrap the smoking article package with the outer wrapper 240. More particularly, in the illustrated embodiment the fourth imaging device 600d is positioned to capture images after enclosing a plurality of smoking articles in the smoking article package, after printing an identifier on the smoking article package, and after wrapping the smoking article package with an outer wrapper, although the images captured may depend on the particular arrangement of the components of the smoking article packaging system 108. The analysis unit 602 may be configured to analyze the images captured by the fourth imaging device 600d to determine whether the smoking article package is defective.

Analyzing the images of the smoking article package may include analyzing images of the packaged smoking articles 102 during or after wrapping packed smoking article packages 236 with the outer wrapper 240. In this regard, in one embodiment the analysis unit 602 may be configured to determine whether the outer wrapper 240 is wrinkled, whether the smoking article package is damaged, whether the smoking article package is contaminated, and/or whether the smoking article package is open. However, the analysis unit 602 may be configured to detect various other defects that may be associated with wrapping the outer wrapper 240 on the smoking article package.

The fourth imaging device 600d may include one or more cameras. An example configuration of a first camera 600d1 of the fourth imaging device 600d at or downstream of the wrapping unit 500 is illustrated in FIG. 20. As illustrated, the first camera 600d1 of the fourth imaging device 600d may be positioned proximate a wrapping wheel 502 configured to wrap the printed smoking article package 236 with the outer wrapper 240 (see, e.g., FIG. 4). Accordingly, the one or more strobe lights 604d (see, e.g., FIG. 4) may illuminate the smoking article packages as they pass the first camera 604d1 of the fourth imaging device 600d such that the fourth imaging device may capture one or more images of each smoking article package passing thereby. The fourth imaging device 600d may capture images of the printed smoking article package 236 after sealing the outer wrapper 240 along the sides thereof, but prior to sealing the outer wrapper 240 at the longitudinal ends thereof. Thereby, for example, a side of the outer wrapper 240 may be inspected.

FIGS. 21A-D are images 1400a-d captured by the first camera 600d1 of the fourth imaging device 600d positioned at or downstream of the wrapping unit 500. As shown, the first camera 600d1 of the fourth imaging device 600d may capture images of the outer wrapper 240 at the side 248 of the smoking article package. In particular, the first camera 600d1 of the fourth imaging device 600d captures images of the right sides 248 of a pair of smoking article packages. However, the first camera 600d1 of the fourth imaging device 600d may capture images of the wrapper 240 on various other portions of the smoking article package and/or images of a lesser or greater number of smoking article packages.

Figure 21A:
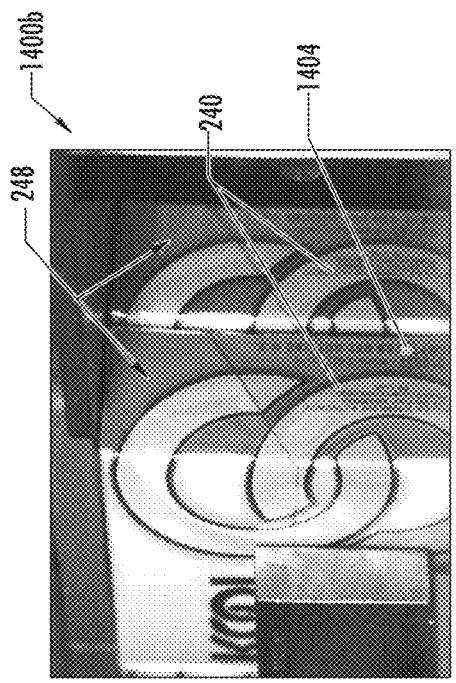
Figure 21B:
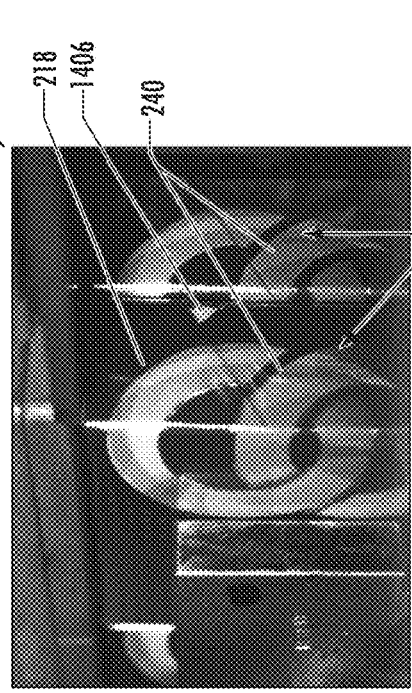
Figure 21C:
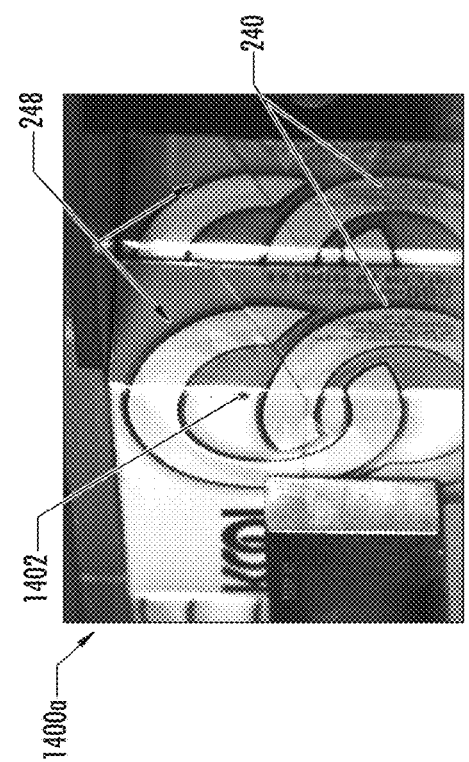
Figure 21D:
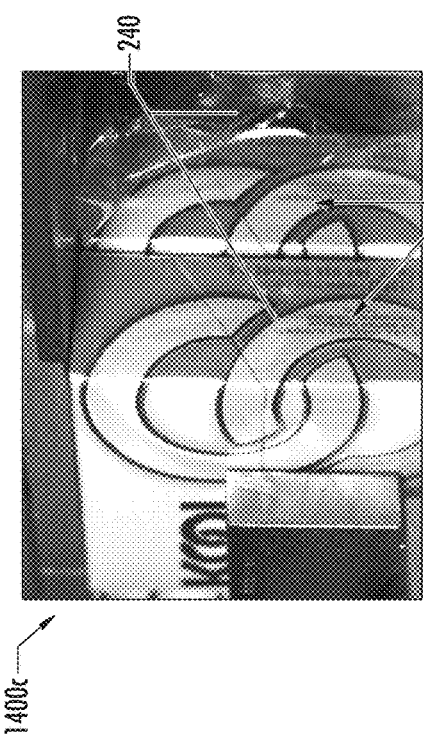

The images 1400a-d of smoking article packages include defects which the analysis unit 602 may detect. In this regard, FIGS. 21A and 21B illustrate images 1400a, b in which the smoking article package is contaminated by debris 1402, 1404 (e.g., tobacco or dirt under the wrapper 240). FIG. 21C illustrates an image 1400c in which the outer wrapper 240 is wrinkled. FIG. 21D illustrates an image 1400d in which the smoking article package is open at a location 1406 below an ear of the lid 218.

In some embodiments the fourth imaging device 600d may include additional or alternative cameras. In this regard, an example configuration of a second camera 600d2 of the fourth imaging device 600d at or downstream of the wrapping unit 500 is illustrated in FIG. 22. As illustrated, the second camera 600d2 of the fourth imaging device 600d may be positioned proximate a rotating wheel or turret 504. The turret 504 may be positioned immediately downstream of a sealing device that seals the outer wrapper 240 at the longitudinal ends of the smoking article package to completely seal the outer wrapper about the packed and printed smoking article package 236 (see, e.g., FIG. 4). Accordingly, the one or more strobe lights 604d (see, e.g., FIG. 4) may illuminate the smoking article packages as they pass the second camera 604d2 of the fourth imaging device 600d such that the imaging device may capture one or more images of each smoking article package passing thereby. Thus, images of the outer wrapper 240 may be captured following completion of the sealing thereof.

FIGS. 23A-D are images 1500a-d captured by the second camera 600d2 of the fourth imaging device 600d positioned at or downstream of the wrapping unit 500. As shown, the second camera 600d2 of the fourth imaging device 600d may capture images of the outer wrapper 240 at the left side 246 of the smoking article package opposing the side 248 of the smoking article package captured by the first camera 600d1. In particular, the second camera 600d2 of the fourth imaging device 600d captures images of the sides 246 of a pair of smoking article packages. However, the second camera 600d2 of the fourth imaging device 600d may capture images of the wrapper 240 on various other portions of the smoking article package and/or images of a lesser or greater number of smoking article packages.

The images 1500a-d of smoking article packages include defects which the analysis unit 602 may detect. In this regard, FIGS. 23A and 23D illustrate images 1500a, d in which the outer wrapper 240 is wrinkled. FIG. 23B illustrates an image 1500b in which the side 246 of one of the smoking article packages is open. FIG. 23C illustrates an image in which the smoking article package is damaged at an ear of the lid 218. Accordingly, images may be captured by the first camera 600d1 and/or the second camera 600d2 of the fourth imaging device 600d positioned at or downstream of the wrapping unit 500 and the images may be analyzed by the analysis unit 602 to detect defects such as those shown in 21A-D and 23A-D.

As illustrated in FIG. 4, in some embodiments a heated air unit 1600 may be provided. As illustrated, the heated air unit 1600 may comprise a chamber 1602 that receives air through an inlet 1604 and directs the air through a nozzle 1606 toward the outer wrapper 240 of a smoking article package. In one embodiment the air may be heated and/or pressurized in the heated air unit 1600 (e.g., via an internal fan and heater). In another embodiment the air may be heated and/or pressurized prior to entering the inlet 1604 (e.g., via an external fan and heater).

The heated air unit 1600 may be configured to direct a flow of heated air at the smoking article packages passing thereby in order to improve the fit of the outer wrapper 240 on the smoking article package. In this regard, the outer wrapper 240 may comprise a material such as cellophane that permanently shrinks when exposed to heat exceeding a specified temperature. Accordingly, the heated air unit 1600 may direct a flow of heated air at the smoking article package to shrink the outer wrapper 240 about the smoking article package. Accordingly, wrinkles in the outer wrapper 240 may be reduced or removed. In one embodiment the temperature or duration of the heated air exposed to the outer wrapper 240 may be adjusted based on the detected presence or amount of wrinkles. In one embodiment the presence or amount of wrinkles may be determined by the analysis unit 602 using images captured by the fourth imaging device 600d.

A controller may be configured to control the temperature of the air directed at the packaged smoking articles 102. Too little heat may result in insufficient wrinkle reduction, whereas too much heat may result in melting of the outer wrapper 240. In this regard, Applicants have determined that for best results, the heated flow may be applied equally to both sides of a single smoking article package at temperatures up to about 130 degrees centigrade from about 150 milliseconds to about 300 milliseconds.

The heated air unit 1600 may be located at a variety of locations at or downstream of the wrapping unit 500. For example, FIG. 24 illustrates a first embodiment of the heated air unit 1600a that is positioned after the wrapping wheel 502 and prior to a double pack position at the turret 504 in which the smoking article packages are stacked on top of one another. In this regard, in one embodiment the heated air unit 1600a may be configured to direct a flow of heated air at an individual packaged smoking article 102. Further, in this position, the heated air unit 1600a may be configured to shrink the outer wrapper 240 after sealing the outer wrapper at the sides of the smoking article package and prior to sealing the outer wrapper at the longitudinal ends of the smoking article package. However, as illustrated in FIG. 25, in another embodiment a heated air unit 1600b may be located at a position at which both the side and longitudinal end seals of the outer wrapper 240 are complete, in order to shrink the wrapper following completion of securement of the wrapper about the smoking article package. For example, as illustrated in FIG. 25, the heated air unit 1600b may be positioned at the turret 504 at which two of the packaged smoking articles 102 are stacked on top of one another prior to placement in cartons by a cartoner.

In other embodiments, images may be captured by imaging devices positioned upstream and/or downstream of the locations disclosed herein. In this regard, for example, images of the smoking articles may be captured prior to the smoking article being packed in the smoking article package, images of the materials defining the smoking article package may be captured prior to formation into a smoking article package, and/or images of the smoking article packages during and/or after insertion into a carton may be captured. As described above, the images may be analyzed by the analysis unit to determine whether the items captured in the images are defective.

As described above, images may be captured at various stages during the production of the packaged smoking articles 102. These images may be analyzed, substantially in real-time, by the analysis unit 602. Accordingly, defects in the smoking article packages may be detected during or substantially immediately following the packing, printing, and wrapping operations.

The analysis unit 602 may analyze the images in a variety of manners in order to determine whether the smoking article packages include defects. For example, the analysis unit 602 may include or be in communication with a database of stored images of defective smoking article packages which may occur during the above-described packing, printing and wrapping operations. In this embodiment, the analysis unit 602 may compare the one or more images captured by the imaging devices 600a-d to the stored images of defective smoking article packages from the database. As such, if the analysis unit 602 matches an image of a smoking article package captured by one of the imaging devices 600a-d to a stored image of a defective smoking article package, to a reasonable certainty, then the particular smoking article package may be determined to be defective.

In another example, the analysis unit 602 may include or be in communication with a database of stored images of one or more non-defective (e.g., properly packed, printed, and/or wrapped) smoking article packages. In those instances, the one or more images of the smoking article package being inspected may then be compared to the stored images of the non-defective smoking article packages by the analysis unit 602. As such, if the analysis unit 602 does not match the one or more images of a smoking article package captured by the imaging devices 600a-d to one of the stored images of the non-defective smoking article packages, to a reasonable certainty, then the particular smoking article package may be determined to be defective.

Note that in the above-described embodiments, the analysis unit 602 may compare the images of the smoking article package captured by the imaging devices 600a-d to stored images based on the particular location at which the images are captured, and thus the images may be compared to smoking article packages in the same state of completion. For example, images of packed and printed smoking article packages captured downstream of the printing unit 400 may be compared to stored images of packed and printed smoking article packages with identifiers printed thereon. Further, the analysis unit 602 may compare each captured image to the stored images based on the particular portion and perspective of the smoking article package captured by the imaging device. In this regard, for example, a smoking article package in a particular stage of completion may have images captured of multiple sides thereof. Thus, the analysis unit 602 may select the stored images with which to compare the captured images based on the location and position of the imaging devices 600a-d capturing the images relative to the smoking article packages.

However, the analysis unit 602 may employ various other techniques and methods in determining whether a smoking article package is defective. For example, the analysis unit 602 may perform optical character recognition (OCR) analysis/evaluation on the one or more images captured by the imaging devices 600a-d. Thus, the identifier may be analyzed by the analysis unit to determine whether it is defective (e.g., illegible, missing print, misaligned, of poor quality, or includes incorrect information).

The analysis unit 602 may additionally or alternatively employ a perimeter edge location tool to determine a position of the smoking article package to determine whether the actual location of portions of the smoking article package match expected (e.g., intended) locations of portions of the smoking article package. For example, the edge location tool may analyze the location of the sides 246, 248 of the smoking article package in relation to an expected position of the sides of the smoking article package. Various other inspection methods and apparatuses which may be employed in the present system are disclosed, for example, in U.S. Patent Application Publication Nos. 2010/0059074, 2011/0169942, and 2012/0120229 to Brantley et al. and 2013/0096711 to Gates et al., each of which is incorporated herein by reference in its entirety. Accordingly, the above-described methods and techniques, in addition to various other methods and techniques may be employed to analyze the images to determine whether smoking article packages are defective.

In some embodiments one or more rejecting units may additionally be provided. As illustrated in FIG. 4, in some embodiments the rejecting unit 1700 may comprise part of the smoking article inspection system 108. However, the rejecting unit 1700 may additionally or alternatively be embodied as a part of the smoking article packaging system 108. Regardless of the particular implementation, the rejecting unit 1700 may be configured to reject a smoking article package when the analysis unit 602 determines that the smoking article package is defective. Accordingly, defective smoking article packages 1702 may be removed, whereas non-defective smoking article packages 1704 may continue to additional production and/or distribution operations.

The defective smoking article packages 1702 may be removed at any point following the capture of an image thereof with one of the imaging devices 600a-d. In this regard, the defective smoking article packages 1702 may be removed by the rejecting unit 1700 after the packing unit 300 packs the smoking articles in the smoking article package, after the printing unit 400 prints an identifier on the smoking article package, and/or after the wrapping unit 500 wraps the smoking article package with an outer wrapper. Accordingly, the rejecting units may include a rejecting unit positioned at or downstream of the packing unit 300 and upstream of the printing unit 400; a rejecting unit positioned at or downstream of the printing unit and upstream of the wrapping unit 500; and/or a rejecting unit positioned at or downstream of the wrapping unit.

The particular method by which the defective smoking article packages 1702 are removed by the rejecting unit 1700 may also vary. For example, a plunger device controlled by a solenoid valve may be employed as described in U.S. Patent Application Publication No. 2012/0120229, to Brantley et al., which is incorporated herein by reference in its entirety. However, the rejecting unit 1700 may employ various other embodiments of removal methods and devices to remove the defective smoking article packages 1702.

By way of example, FIGS. 7-9 illustrate a rejecting unit 1700b positioned downstream of the second imaging device 600b. As illustrated, the casing 606 may at least partially define a chute 618 configured to receive defective packed smoking article packages. In this regard, after a packed and printed smoking article package 236 is determined to be defective at the second imaging device 600b, compressed air may be released from a manifold 620 (see, FIG. 9) and directed at the top 244 of one of the packed and printed smoking article packages such that the smoking article package is pushed out of the delivery conduit 610 and into the chute 618. Further, when a defective packed and printed smoking article package is detected, a light 622 may illuminate to inform an operator that a defective smoking article package is being removed, such that the operator may be informed of the rejection and optionally inspect the packed smoking article package further.

By way of further example, FIGS. 11-14 illustrate a rejecting unit 1700c positioned downstream of the third imaging device 600c. As illustrated, the rejecting unit 1700c may comprise a chute 632 configured to receive defective packed smoking article packages. In this regard, after a packed and printed smoking article package 236 is determined to be defective at the third imaging device 600c, compressed air may be released from a manifold 634 (see, FIG. 14) and directed at the smoking article package (e.g., at the back 252 of the smoking article package) such that it is pushed into the chute 632. In this regard, a sensor 636 (e.g., a light or laser optical sensor) may detect presence of the smoking article package as the conveyor belt 628 transports the smoking article package to the rejecting unit 1700c. Thus, the release of the compressed air by the manifold 634 may be timed to correspond with positioning of the smoking article package 236 in front of the manifold 634.

As noted above, the smoking article inspection system 110 may be provided in combination with a smoking article packaging system 108. In this regard, in one embodiment the analysis unit 602 of the smoking article inspection system may be configured to instruct the smoking article inspection system 110 to stop packaging the smoking articles in certain predetermined circumstances. For example, the analysis unit 602 may instruct the smoking article packaging system 108 to stop packaging the smoking articles when the analysis unit detects a predefined consecutive number of defective smoking article packages (e.g., three to five consecutive defective smoking article packages) detected at a single imaging device, detected at multiple imaging devices, or detected at all of the imaging devices. Accordingly, a problem with the smoking article packaging system 108 resulting in multiple defective smoking article packages may be identified by the analysis unit 602 and the smoking article packaging system may be quickly stopped to prevent wasting significant quantities of materials and inputs.

However, the analysis unit 602 may be configured to instruct the smoking article packaging system 108 to stop under a variety of other circumstances. For example, the analysis unit 602 may instruct the smoking article packaging system 108 to stop when one or more of the imaging devices 600a-d is not capturing images, when a sensor at the rejecting unit 1702 does not detect rejection of a defective smoking article package 1702, when a door at the rejecting unit is open when it is supposed to be closed, when the analysis unit 602 is not in communication with the smoking article packaging system 108, when a camera trigger sensor (e.g., a photocell) does not detect smoking article packages after a predetermined period of time or machine cycles, and/or when any other fault is detected with the smoking article packaging or inspection systems 108, 110.

Thus, as described above, a detected defective smoking article packages may be discarded by one or more rejecting units. Further, operation of the packaging system may be shut down when the defective smoking article packages meet certain thresholds. Additionally, in some embodiments the analysis unit 602 may be configured to determine the one of the operations causing damage to the smoking article package from analysis of the images of the smoking article package captured before and after each of the operations. In this regard, by analyzing the images captured before and after operations are performed thereon, it may be possible to determine which of the operations are damaging the smoking article packages. Accordingly, in addition to identifying defective smoking article packages, it may be possible to identify the source of the defects, such that the cause of the defect may be isolated. Thereby, machinery performing the operations may be adjusted, repaired, or replaced depending on the particular identified cause of the defects.

In some embodiments the analysis unit 602 may be configured to execute computer code in order to perform the above-described functions. In this regard, the analysis unit 602 may comprise a processor that may be a microprocessor or controller for controlling the overall operation thereof. In one embodiment the processor may be particularly configured to perform the functions described herein. The analysis unit 602 may also include a memory device. The memory device may include non-transitory and tangible memory that may be, for example, volatile and/or non-volatile memory. The memory device may be configured to store information, data, files, applications, instructions or the like. For example, the memory device could be configured to buffer input data for processing by the processor. Additionally or alternatively, the memory device may be configured to store instructions for execution by the processor.

The analysis unit 602 may also include a user interface that allows a user to interact therewith. For example, the user interface can take a variety of forms, such as a button, keypad, dial, touch screen, audio input interface, visual/image capture input interface, input in the form of sensor data, etc. Still further, the user interface may be configured to output information to the user through a display, speaker, or other output device. A communication interface may provide for transmitting and receiving data through, for example, a wired or wireless network such as a local area network (LAN), a metropolitan area network (MAN), and/or a wide area network (WAN), for example, the Internet.

A method for inspecting a smoking article package is also provided. As illustrated in FIG. 26, the method may comprise capturing a plurality of images of the smoking article package before and after one or more operations are performed thereon at operation 1802. The operations may include enclosing a plurality of smoking articles in the smoking article package, printing an identifier on the smoking article package, and wrapping the smoking article package with an outer wrapper. Additionally, the method may include analyzing the images to determine whether the smoking article package is defective at operation 1804. Further, the method may include determining one of the operations causing damage to the smoking article package from analysis of the images of the smoking article package captured before and after each of the operations, if the smoking article package is determined to be defective at operation 1806.

In some embodiments, capturing the images of the smoking article package at operation 1802 may comprise capturing the images of the smoking article package at or downstream of a packing unit configured to pack a plurality of smoking articles in the smoking article package. Further, capturing the images of the smoking article package at operation 1802 may comprise capturing the images of the smoking article package at the packing unit. Analyzing the images at operation 1804 may comprise determining, at the packing unit, at least one of: whether the smoking article package is missing an inner frame, whether the inner frame is misaligned, whether the smoking article package is missing an insert, whether the insert is misaligned, and whether an inner wrapper surrounding the smoking articles is damaged.

In some embodiments capturing the images of the smoking article package at operation 1802 may comprise capturing the images of the smoking article package downstream of the packing unit. Analyzing the images at operation 1804 may comprise determining, downstream of the packing unit, at least one of: whether a flap of the smoking article package is open, whether a lid of the smoking article package is open, whether an ear of the smoking article package is open, whether the identifier is illegible, whether the identifier is missing print, whether the identifier is misaligned, whether the identifier is of poor quality, whether the identifier includes incorrect information, whether the smoking article package is damaged, whether the smoking article package is contaminated, and whether the smoking article package is improperly positioned.

In some embodiments capturing the images of the smoking article package at operation 1802 may comprise capturing the images of the smoking article package at or downstream of a printing unit configured to print the identifier. Further, analyzing the images at operation 1804 may comprise determining at least one of: whether the identifier is illegible, whether the identifier is missing print, whether the identifier is misaligned, whether the identifier is of poor quality, whether the identifier includes incorrect information.

In some embodiments capturing the images of the smoking article package at operation 1802 may comprise capturing the images of the smoking article package at or downstream of a wrapping unit configured to wrap the smoking article package with an outer wrapper. Further, analyzing the images at operation 1804 may comprise determining at least one of: whether the outer wrapper is wrinkled, whether the smoking article package is damaged, whether the smoking article package is contaminated, and whether the smoking article package is open.

In some embodiments the method may further comprise packaging a plurality of smoking articles with a smoking article packaging system at operation 1808. Further, the smoking article packaging system may be configured to stop packaging the smoking articles when a predefined consecutive number of defective smoking article packages are detected at operation 1810. Additionally, the method may include illuminating the smoking article package at operation 1812 while capturing the images of the smoking article package. The method may further comprise rejecting the smoking article package when the smoking article package is determined to be defective at operation 1814.

In some embodiments rejecting the smoking article package when the smoking article package is determined to be defective at operation 1814 may comprise rejecting the smoking article package upstream of a printing unit configured to print the identifier when the smoking article package is determined to be defective upstream of the printing unit, rejecting the smoking article package upstream of a wrapping unit configured to wrap the smoking article package with the outer wrapper when the smoking article package is determined to be defective upstream of the wrapping unit, and rejecting the smoking article package downstream of the wrapping unit when the smoking article package is determined to be defective at or downstream of the wrapping unit. Further, analyzing the images to determine whether the smoking article package is defective at operation 1804 may comprise comparing the images captured by the imaging devices to one of a plurality of stored images of defective smoking article packages and a plurality of stored images of non-defective smoking article packages.

Although the present disclosure is generally discussed herein in terms of manufacturing and inspection of smoking article packages, this discussion is provided for example purposes only. In this regard, inspection, analysis, and the various other functions discussed herein may also be applied to other containers and items. For example, the present disclosure is particularly applicable to any process involving packing of products in a container, printing an identifier thereon, and/or wrapping a container.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

What is claimed is:

1. A smoking article package inspection system configured to inspect a smoking article package, the smoking article package inspection system comprising:
   a plurality of imaging devices configured to capture a plurality of images of the smoking article package before and after each of a plurality of operations are performed thereon, the operations including:
   enclosing a plurality of smoking articles in the smoking article package,
   printing an identifier on the smoking article package, and
   wrapping the smoking article package with an outer wrapper; and
   an image data analysis device having a processor and being in communication with the plurality of imaging devices, the image data analysis device being configured to analyze the images captured by the imaging devices to determine whether the smoking article package is defective from the images thereof, and, if the smoking article package is determined to be defective, to determine one of the operations causing damage to the smoking article package from analysis of the images of the smoking article package captured before and after each of the operations.

2. The smoking article package inspection system of claim 1, wherein at least one of the imaging devices is positioned at or downstream of a packing unit configured to pack the smoking articles in the smoking article package, the image data analysis device being configured to analyze the images captured by the at least one of the imaging devices at or downstream of the packing unit.

3. The smoking article package inspection system of claim 2, wherein the at least one of the imaging devices is positioned at the packing unit and the image data analysis device is configured to determine, at the packing unit, at least one of:
   whether the smoking article package is missing an inner frame;
   whether the inner frame is misaligned;
   whether the smoking article package is missing an insert;
   whether the insert is misaligned; and
   whether an inner wrapper surrounding the smoking articles is damaged.

4. The smoking article package inspection system of claim 2, wherein the at least one of the imaging devices is positioned downstream of the packing unit and the image data analysis device is configured to determine, downstream of the packing unit, at least one of:
   whether a flap of the smoking article package is open;
   whether a lid of the smoking article package is open;
   whether an ear of the smoking article package is open;
   whether the identifier is illegible;
   whether the identifier is missing print;
   whether the identifier is misaligned;
   whether the identifier is of poor quality;
   whether the identifier includes incorrect information;
   whether the smoking article package is damaged;
   whether the smoking article package is contaminated; and whether the smoking article package is improperly positioned.

5. The smoking article package inspection system of claim 1, wherein at least one of the imaging devices is positioned at or downstream of a printing unit configured to print the identifier, the image data analysis device being configured to analyze the images captured at or downstream of the printing unit.

6. The smoking article package inspection system of claim 5, wherein the image data analysis device is configured to determine at least one of:
whether the identifier is illegible;
whether the identifier is missing print;
whether the identifier is misaligned;
whether the identifier is of poor quality; and
whether the identifier includes incorrect information.

7. The smoking article package inspection system of claim 1, wherein at least one of the imaging devices is positioned at or downstream of a wrapping unit configured to wrap the smoking article package with an outer wrapper, the image data analysis device being configured to analyze the images captured at or downstream of the wrapping unit.

8. The smoking article package inspection system of claim 7, wherein the image data analysis device is configured to determine at least one of:
whether the outer wrapper is wrinkled;
whether the smoking article package is damaged;
whether the smoking article package is contaminated; and
whether the smoking article package is open.

9. The smoking article inspection system of claim 1, further comprising one or more strobe lights, the strobe lights being configured to illuminate the smoking article package at the imaging devices.

10. The smoking article inspection system of claim 1, in combination with a smoking article packaging system having a packing unit configured to package a plurality of smoking articles, wherein the smoking article packaging system is configured to stop packaging the smoking articles when the image data analysis device detects a predefined consecutive number of defective smoking article packages.

11. The smoking article inspection system of claim 1, further comprising one or more rejecting units positioned downstream of at least one of the plurality of imaging devices, the one or more rejecting units being configured to reject the smoking article package if the image data analysis device determines that the smoking article package is defective.

12. The smoking article inspection system of claim 11, wherein the rejecting units include:
a rejecting unit positioned at or downstream of a packing unit configured to pack the smoking articles in the smoking article package and upstream of a printing unit configured to print the identifier;
a rejecting unit positioned at or downstream of the printing unit and upstream of a wrapping unit configured to wrap the smoking article package with the outer wrapper; and
a rejecting unit positioned at or downstream of the wrapping unit.

13. The smoking article inspection system of claim 1, wherein the image data analysis device is configured to compare the images captured by the imaging devices to one of a plurality of stored images of defective smoking article packages and a plurality of stored images of non-defective smoking article packages to determine whether the smoking article package is defective.

14. A method for inspecting a smoking article package, the method comprising:
capturing a plurality of images of the smoking article package before and after each of a plurality of operations are performed thereon, the operations including:
enclosing a plurality of smoking articles in the smoking article package,
printing an identifier on the smoking article package, and
wrapping the smoking article package with an outer wrapper;
analyzing the images to determine whether the smoking article package is defective; and
determining one of the operations causing damage to the smoking article package from analysis of the images of the smoking article package captured before and after each of the operations, if the smoking article package is determined to be defective.

15. The method of claim 14, wherein capturing the images of the smoking article package comprises capturing the images of the smoking article package at or downstream of a packing unit configured to pack a plurality of smoking articles in the smoking article package.

16. The method of claim 15, wherein capturing the images of the smoking article package comprises capturing the images of the smoking article package at the packing unit, and wherein analyzing the images comprises determining, at the packing unit, at least one of:
whether the smoking article package is missing an inner frame;
whether the inner frame is misaligned;
whether the smoking article package is missing an insert;
whether the insert is misaligned; and
whether an inner wrapper surrounding the smoking articles is damaged.

17. The method of claim 15, wherein capturing the images of the smoking article package comprises capturing the images of the smoking article package downstream of the packing unit, and wherein analyzing the images comprises determining, downstream of the packing unit, at least one of:
whether a flap of the smoking article package is open;
whether a lid of the smoking article package is open;
whether an ear of the smoking article package is open;
whether the identifier is illegible;
whether the identifier is missing print;
whether the identifier is misaligned;
whether the identifier is of poor quality;
whether the identifier includes incorrect information;
whether the smoking article package is damaged;
whether the smoking article package is contaminated; and
whether the smoking article package is improperly positioned.

18. The method of claim 14, wherein capturing the images of the smoking article package comprises capturing the images of the smoking article package at or downstream of a printing unit configured to print the identifier.

19. The method of claim 18, wherein analyzing the images comprises determining at least one of:
whether the identifier is illegible;
whether the identifier is missing print;
whether the identifier is misaligned;
whether the identifier is of poor quality; and
whether the identifier includes incorrect information.

20. The method of claim 14, wherein capturing the images of the smoking article package comprises capturing the images of the smoking article package at or downstream of a wrapping unit configured to wrap the smoking article package with an outer wrapper.

21. The method of claim 20, wherein analyzing the images comprises determining at least one of:
whether the outer wrapper is wrinkled;
whether the smoking article package is damaged;
whether the smoking article package is contaminated; and
whether the smoking article package is open.

22. The method of claim 14, further comprising illuminating the smoking article package while capturing the images of the smoking article package.

23. The method of claim 14, further comprising packaging a plurality of smoking articles with a smoking article packaging system, the smoking article packaging system being configured to stop packaging the smoking articles when a predefined consecutive number of defective smoking article packages are detected.

24. The method of claim 14, further comprising rejecting the smoking article package when the smoking article package is determined to be defective.

25. The method of claim 24, wherein rejecting the smoking article package when the smoking article package is determined to be defective comprises:

rejecting the smoking article package upstream of a printing unit configured to print the identifier when the smoking article package is determined to be defective upstream of the printing unit;

rejecting the smoking article package upstream of a wrapping unit configured to wrap the smoking article package with the outer wrapper when the smoking article package is determined to be defective upstream of the wrapping unit; and rejecting the smoking article package downstream of the wrapping unit when the smoking article package is determined to be defective at or downstream of the wrapping unit.

26. The method of claim 14, wherein analyzing the images to determine whether the smoking article package is defective comprises comparing the images captured by the imaging devices to one of a plurality of stored images of defective smoking article packages and a plurality of stored images of non-defective smoking article packages.

* * * * *